(12) United States Patent
Zlatev et al.

(10) Patent No.: US 9,035,041 B2
(45) Date of Patent: May 19, 2015

(54) PROCESS FOR TRIPHOSPHATE OLIGONUCLEOTIDE SYNTHESIS

(75) Inventors: Ivan Zlatev, Cambridge, MA (US); Francois Morvan, Paris (FR); Jean-Jacques Vasseur, Paris (FR); Francoise Debart, Paris (FR); Muthiah Manoharan, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 252 days.

(21) Appl. No.: 13/393,851

(22) PCT Filed: Dec. 22, 2009

(86) PCT No.: PCT/US2009/069201
§ 371 (c)(1), (2), (4) Date: May 14, 2012

(87) PCT Pub. No.: WO2011/028218
PCT Pub. Date: Mar. 10, 2011

(65) Prior Publication Data
US 2012/0220761 A1    Aug. 30, 2012

(51) Int. Cl.
*C07H 21/00* (2006.01)
*C12N 15/117* (2010.01)

(52) U.S. Cl.
CPC .............. *C07H 21/00* (2013.01); *C12N 15/117* (2013.01); *C12N 2310/17* (2013.01); *C12N 2310/321* (2013.01)

(58) Field of Classification Search
CPC ...................................................... C07H 21/00
See application file for complete search history.

(56) References Cited

U.S. PATENT DOCUMENTS

| 6,320,035 | B1 * | 11/2001 | Muhlegger et al. | 536/23.1 |
| 7,759,469 | B2 * | 7/2010 | Heindl et al. | 536/4.1 |
| 2005/0119214 | A1 | 6/2005 | Manoharan et al. | |

FOREIGN PATENT DOCUMENTS

| WO | WO 88/10264 A1 * | 12/1988 |
| WO | 2011028218 A1 | 3/2011 |

OTHER PUBLICATIONS

Burgess and Cook, "Syntheses of Nucleoside Triphosphates" Chem. Rev. 100:2047-59 (2000).
Cook et al., "Nucleoside S-Alkyl Phosphorothioates .III. Application to Oligonuclotide Synthesis" J. Am. Chem. Soc. 91(23):6479-84 (1969).
Lebedev et al., "Preparation of Oligodeoxynuvleotide 5'-Triphosphates Using Solid Support Approach", Nucleos. Nucleot. Nucl. 20(4-7):1403-09 (2001).
Sun et al., "One-Pot Synthesis of Nucleoside 5'-Triphosphates From Nucleoside 5'Hphosphonates" Org. Lett. 10(9)1 703-06 (2008).
Zlatev et al., "Delta-Di-Carboxybutyl Phosphoramidate of 2'-Deoxycytidine-5'-Monophosphate As Substrate for DNA Polymerization by HIV-1 Reverse Transcriptase" Bioorgan. Med. Chem. 17:7008-14 (2009).
Zlatev et al., "Efficient Solid-Phase Chemical Synthesis of 5'-Triphosphates of DNA, RNA, and Their Analogues" Org. Lett 12(10):2190-93 (2010).

* cited by examiner

*Primary Examiner* — Lawrence E Crane
(74) *Attorney, Agent, or Firm* — LeClairRyan; Jeffrey N. Townes; Hongling Zou

(57) ABSTRACT

This invention relates to a process for preparing an oligonucleotide 5'-triphosphate. The process comprises the steps of: (a) synthesizing an oligonucleotide having a 5' hydroxyl moiety; (b) reacting the 5' hydroxyl moiety with a reagent of formula I:

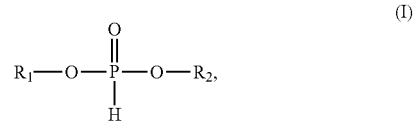

to convert the 5' hydroxyl moiety to a 5'-H-phosphonate, wherein $R_1$ and $R_2$ are each independently selected from the group consisting of haloalkyl, aryl, substituted aryl, heteroaryl, substituted heteroaryl, cycloalkyl, substituted cycloalkyl, heterocycle, and substituted heterocycle, acyl, phosphoryl, substituted alkyl acyl, substituted heteroalkyl acyl, substituted aryl acyl or substituted heteroaryl acyl, substituted alkyl phosphoryl, substituted heteroalkyl acyl, substituted aryl phosphoryl, and substituted heteroaryl phosphoryl; (c) activating the H-phosphonate of step (b) by reacting the H-phosphonate with a silylating agent, a halogenated oxidizing agent, a nitrogen-containing heteroaryl, or a combination thereof, to form an activated H-phosphonate; and (d) treating the oligonucleotide having an activated H-phosphonate from step (c) with a poly(alkylammonium)pyrophosphate.

21 Claims, 4 Drawing Sheets

SEQUENCE LISTING

```
<160> NUMBER OF SEQ ID NOS: 17

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uugucucugg uccuuacuua a                                                   21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: 5'-triphosphate modification

<400> SEQUENCE: 2
uugucucugg uccuuacuua a                                                   21

<210> SEQ ID NO 3
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: 5'-triphosphate modification

<400> SEQUENCE: 3
aguuguuccc                                                                10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: This sequence may encompass 1-10 bases
```

```
<400> SEQUENCE: 4
tttttttttt                                                                10

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(1)
<223> OTHER INFORMATION: 5'-triphosphate modification
<220> FEATURE:
<221> NAME/KEY: misc_feature
<222> LOCATION: (20)..(21)
<223> OTHER INFORMATION: Phosphorothioate linkage

<400> SEQUENCE: 5
aaguaaggac cagagacaat t                                                   21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(1)
<223> OTHER INFORMATION: 5'-triphosphate modification
<220> FEATURE:
<221> NAME/KEY: modified_base
<222> LOCATION: (2)..(3)
<223> OTHER INFORMATION: 2'-O-Me modified base
<220> FEATURE:
<221> NAME/KEY: modified_base
<222> LOCATION: (8)..(8)
<223> OTHER INFORMATION: 2'-O-Me modified base
<220> FEATURE:
<221> NAME/KEY: modified_base
<222> LOCATION: (10)..(11)
<223> OTHER INFORMATION: 2'-O-Me modified base
<220> FEATURE:
<221> NAME/KEY: modified_base
<222> LOCATION: (13)..(15)
<223> OTHER INFORMATION: 2'-O-Me modified base
<220> FEATURE:
<221> NAME/KEY: modified_base
<222> LOCATION: (17)..(19)
<223> OTHER INFORMATION: 2'-O-Me modified base
<220> FEATURE:
<221> NAME/KEY: misc_feature
<222> LOCATION: (20)..(21)
<223> OTHER INFORMATION: Phosphorothioate linkage

<400> SEQUENCE: 6
accgaagugu uguuugucct t                                                   21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
         oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(1)
<223> OTHER INFORMATION: 5'-triphosphate modification
<220> FEATURE:
<221> NAME/KEY: modified_base
<222> LOCATION: (1)..(19)
<223> OTHER INFORMATION: 2'-O-Me modified base
<220> FEATURE:
<221> NAME/KEY: misc_feature
<222> LOCATION: (20)..(21)
<223> OTHER INFORMATION: Phosphorothioate linkage

<400> SEQUENCE: 7
aaguaaggac cagagacaat t                                              21

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tttttttttt                                                           10

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(19)
<223> OTHER INFORMATION: 2'-O-Me modified base
<220> FEATURE:
<221> NAME/KEY: misc_feature
<222> LOCATION: (20)..(21)
<223> OTHER INFORMATION: Phosphorothioate linkage

<400> SEQUENCE: 9
aacgaagugu uguuugucct t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'OTBDMS modified base
<220> FEATURE:
<221> NAME/KEY: modified_base
<222> LOCATION: (2)..(3)
<223> OTHER INFORMATION: 2'-O-Me modified base
<220> FEATURE:
<221> NAME/KEY: modified_base
```

```
<222> LOCATION: (4)..(7)
<223> OTHER INFORMATION: 2'OTBDMS modified base
<220> FEATURE:
<221> NAME/KEY: modified_base
<222> LOCATION: (8)..(8)
<223> OTHER INFORMATION: 2'-O-Me modified base
<220> FEATURE:
<221> NAME/KEY: modified_base
<222> LOCATION: (9)..(9)
<223> OTHER INFORMATION: 2'OTBDMS modified base
<220> FEATURE:
<221> NAME/KEY: modified_base
<222> LOCATION: (10)..(11)
<223> OTHER INFORMATION: 2'-O-Me modified base
<220> FEATURE:
<221> NAME/KEY: modified_base
<222> LOCATION: (12)..(12)
<223> OTHER INFORMATION: 2'OTBDMS modified base
<220> FEATURE:
<221> NAME/KEY: modified_base
<222> LOCATION: (13)..(15)
<223> OTHER INFORMATION: 2'-O-Me modified base
<220> FEATURE:
<221> NAME/KEY: modified_base
<222> LOCATION: (16)..(16)
<223> OTHER INFORMATION: 2'OTBDMS modified base
<220> FEATURE:
<221> NAME/KEY: modified_base
<222> LOCATION: (17)..(19)
<223> OTHER INFORMATION: 2'-O-Me modified base
<220> FEATURE:
<221> NAME/KEY: misc_feature
<222> LOCATION: (20)..(21)
<223> OTHER INFORMATION: Phosphorothioate linkage

<400> SEQUENCE: 10
accgaagugu uguuugucct t                                          21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'OTBDMS modified base

<400> SEQUENCE: 11
uugucucugg uccuuacuua a                                          21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Me modified base
<220> FEATURE:
<221> NAME/KEY: modified_base
<222> LOCATION: (2)..(2)
<223> OTHER INFORMATION: 2'fluoro modified base
<220> FEATURE:
<221> NAME/KEY: modified_base
<222> LOCATION: (3)..(3)
<223> OTHER INFORMATION: 2'-O-Me modified base
<220> FEATURE:
<221> NAME/KEY: modified_base
<222> LOCATION: (4)..(4)
```

```
<223> OTHER INFORMATION: 2'fluoro modified base
<220> FEATURE:
<221> NAME/KEY: modified_base
<222> LOCATION: (5)..(5)
<223> OTHER INFORMATION: 2'-O-Me modified base
<220> FEATURE:
<221> NAME/KEY: modified_base
<222> LOCATION: (6)..(6)
<223> OTHER INFORMATION: 2'fluoro modified base
<220> FEATURE:
<221> NAME/KEY: modified_base
<222> LOCATION: (7)..(7)
<223> OTHER INFORMATION: 2'-O-Me modified base
<220> FEATURE:
<221> NAME/KEY: modified_base
<222> LOCATION: (8)..(8)
<223> OTHER INFORMATION: 2'fluoro modified base
<220> FEATURE:
<221> NAME/KEY: modified_base
<222> LOCATION: (9)..(9)
<223> OTHER INFORMATION: 2'-O-Me modified base
<220> FEATURE:
<221> NAME/KEY: modified_base
<222> LOCATION: (10)..(10)
<223> OTHER INFORMATION: 2'fluoro modified base
<220> FEATURE:
<221> NAME/KEY: modified_base
<222> LOCATION: (11)..(11)
<223> OTHER INFORMATION: 2'-O-Me modified base
<220> FEATURE:
<221> NAME/KEY: modified_base
<222> LOCATION: (12)..(12)
<223> OTHER INFORMATION: 2'fluoro modified base
<220> FEATURE:
<221> NAME/KEY: modified_base
<222> LOCATION: (13)..(13)
<223> OTHER INFORMATION: 2'-O-Me modified base
<220> FEATURE:
<221> NAME/KEY: modified_base
<222> LOCATION: (14)..(14)
<223> OTHER INFORMATION: 2'fluoro modified base
<220> FEATURE:
<221> NAME/KEY: modified_base
<222> LOCATION: (15)..(15)
<223> OTHER INFORMATION: 2'-O-Me modified base
<220> FEATURE:
<221> NAME/KEY: modified_base
<222> LOCATION: (16)..(16)
<223> OTHER INFORMATION: 2'fluoro modified base
<220> FEATURE:
<221> NAME/KEY: modified_base
<222> LOCATION: (17)..(17)
<223> OTHER INFORMATION: 2'-O-Me modified base
<220> FEATURE:
<221> NAME/KEY: modified_base
<222> LOCATION: (18)..(18)
<223> OTHER INFORMATION: 2'fluoro modified base
<220> FEATURE:
<221> NAME/KEY: modified_base
<222> LOCATION: (19)..(19)
<223> OTHER INFORMATION: 2'-O-Me modified base
<220> FEATURE:
<221> NAME/KEY: modified_base
<222> LOCATION: (20)..(20)
<223> OTHER INFORMATION: 2'fluoro modified base
<220> FEATURE:
<221> NAME/KEY: modified_base
<222> LOCATION: (21)..(21)
<223> OTHER INFORMATION: 2'-O-Me modified base

<400> SEQUENCE: 12
uugucucugg uccuuacuua a                                         21

<210> SEQ ID NO 13
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Me modified base
<220> FEATURE:
<221> NAME/KEY: modified_base
<222> LOCATION: (2)..(2)
<223> OTHER INFORMATION: 2'OTBDMS modified base
<220> FEATURE:
<221> NAME/KEY: modified_base
<222> LOCATION: (3)..(3)
<223> OTHER INFORMATION: 2'-O-Me modified base
<220> FEATURE:
<221> NAME/KEY: modified_base
<222> LOCATION: (4)..(4)
<223> OTHER INFORMATION: 2'OTBDMS modified base
<220> FEATURE:
<221> NAME/KEY: modified_base
<222> LOCATION: (5)..(5)
<223> OTHER INFORMATION: 2'-O-Me modified base
<220> FEATURE:
<221> NAME/KEY: modified_base
<222> LOCATION: (6)..(6)
<223> OTHER INFORMATION: 2'OTBDMS modified base
<220> FEATURE:
<221> NAME/KEY: modified_base
<222> LOCATION: (7)..(7)
<223> OTHER INFORMATION: 2'-O-Me modified base
<220> FEATURE:
<221> NAME/KEY: modified_base
<222> LOCATION: (8)..(8)
<223> OTHER INFORMATION: 2'OTBDMS modified base
<220> FEATURE:
<221> NAME/KEY: modified_base
<222> LOCATION: (9)..(9)
<223> OTHER INFORMATION: 2'-O-Me modified base
<220> FEATURE:
<221> NAME/KEY: modified_base
<222> LOCATION: (10)..(10)
<223> OTHER INFORMATION: 2'OTBDMS modified base
<220> FEATURE:
<221> NAME/KEY: modified_base
<222> LOCATION: (11)..(11)
<223> OTHER INFORMATION: 2'-O-Me modified base
<220> FEATURE:
<221> NAME/KEY: modified_base
<222> LOCATION: (12)..(12)
<223> OTHER INFORMATION: 2'OTBDMS modified base
<220> FEATURE:
<221> NAME/KEY: modified_base
<222> LOCATION: (13)..(13)
<223> OTHER INFORMATION: 2'-O-Me modified base
<220> FEATURE:
<221> NAME/KEY: modified_base
<222> LOCATION: (14)..(14)
<223> OTHER INFORMATION: 2'OTBDMS modified base
<220> FEATURE:
<221> NAME/KEY: modified_base
<222> LOCATION: (15)..(15)
<223> OTHER INFORMATION: 2'-O-Me modified base
<220> FEATURE:
<221> NAME/KEY: modified_base
<222> LOCATION: (16)..(16)
<223> OTHER INFORMATION: 2'OTBDMS modified base
<220> FEATURE:
<221> NAME/KEY: modified_base
<222> LOCATION: (17)..(17)
<223> OTHER INFORMATION: 2'-O-Me modified base
<220> FEATURE:
<221> NAME/KEY: modified_base
<222> LOCATION: (18)..(18)
<223> OTHER INFORMATION: 2'OTBDMS modified base
<220> FEATURE:
<221> NAME/KEY: modified_base
<222> LOCATION: (19)..(19)
<223> OTHER INFORMATION: 2'-O-Me modified base
```

-continued

```
<220> FEATURE:
<221> NAME/KEY: modified_base
<222> LOCATION: (20)..(20)
<223> OTHER INFORMATION: 2'OTBDMS modified base
<220> FEATURE:
<221> NAME/KEY: modified_base
<222> LOCATION: (21)..(21)
<223> OTHER INFORMATION: 2'-O-Me modified base

<400> SEQUENCE: 13 ugucucugg uccuuacuua a                                          21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'OTBDMS modified base

<400> SEQUENCE: 14 ugucucugg uccuuacuua a                                          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(19)
<223> OTHER INFORMATION: 2'OTBDMS modified base
<220> FEATURE:
<221> NAME/KEY: misc_feature
<222> LOCATION: (20)..(21)
<223> OTHER INFORMATION: Phosphorothioate linkage

<400> SEQUENCE: 15
aaguaaggac cagagacaat t                                         21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(19)
<223> OTHER INFORMATION: 2'-O-Me modified base
<220> FEATURE:
<221> NAME/KEY: misc_feature
<222> LOCATION: (20)..(21)
<223> OTHER INFORMATION: Phosphorothioate linkage

<400> SEQUENCE: 16
aaguaaggac cagagacaat t                                         21
```

```
<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
1               5
```

PROCESS FOR TRIPHOSPHATE OLIGONUCLEOTIDE SYNTHESIS

REFERENCE TO RELATED APPLICATIONS

This application claims priority to PCT Application No. PCT/US2009/069201, filed Dec. 22, 2009, which claims the benefit of priority to PCT Application PCT/US2009/055775, filed Sep. 2, 2009, all of which are hereby incorporated by reference in their entirety.

TECHNICAL FIELD

The present invention describes simple, efficient, and enzyme-free methods of making oligonucleotides with 5'-triphosphate. This invention presents novel processes for synthesizing triphosphate oligonucleotides using diaryl phosphite as a reagent. The process of the present invention are amenable to large-scale, economic 5'-triphosphate oligonucleotide synthesis.

BACKGROUND

Oligonucleotide 5'-triphosphates (ONTPs) are not commercially available; still they find a great number of important biochemical applications: DNA ONTPs are used in the antisense field, in basic research or in the biotechnology industry (Brownlee, et al., *Nucleic Acids Research* 1995, 23, (14), 2641-2647)), as substrates for polymerases or ligases in the preparation of synthetic genes (Xiong, et al., *Fems Microbiology Reviews* 2008, 32, (3), 522-540); various synthetic RNA ONTPs can be used as primers for the amplification of RNA molecules by a 5'-pyrophosphate activated, template directed oligoribonucleotide ligation—either catalyzed by RNA ligases or non enzymatic; but also in detection of viral responses via activation of the RIG-I protein; induction of antiviral immunity (Joyce, et al., *Angewandte Chemie-International Edition* 2007, 46, (34), 6420-6436; Ekland, et al., *Science* 1995, 269, (5222), 364-370; Rohatgi, et al., *Journal of the American Chemical Society* 1996, 118, (14), 3340-3344; Hornung, et al., *Science* 2006, 314, (5801), 994-997; Allam, et al. *Eur J Immunol* 2008); or for their enzymatic conversion to 5'-capped RNAs (Brownlee, et al., *Nucleic Acids Research* 1995, 23, (14), 2641-2647); Olsen, et al. *Journal of Biological Chemistry* 1996, 271, (13), 7435-7439), the latter being useful for the determination of particular viral sequences, for the biochemical characterization of specific cap enzymes and the associated mRNA cap complexes, in order to study the translation mechanisms (Peyrane, et al., *Nucleic Acids Research* 2007, 35, (4)). Moreover, as recently reported (Poeck, et al., *Nat Med* 2008, 14, (11), 1256-63), the triggered immune response following 5'-triphosphate RNA binding to RIG-I synergized with oligonucleotide-mediated gene silencing, to cause massive apoptosis in tumor cells by using 5'-triphosphate oligonucleotide as a single molecule double-targeted treatment. This data can only suggest about the high therapeutic potential of immunostimulatory nucleic acids to be exploited in the future (Barchet et al., *Curr Opin Immunol* 2008, 20, (4), 389-95). In addition, very recent insights in the nature of the controversial RIG-I substrate-type could be brought into light thanks to the use of synthetic RNA ONTPs instead of the 5'-triphosphorylated products generated by in vitro RNA transcription (Ujita, et al. *Immunity* 2009, 31, (1), 4-5; Schlee et al., *Immunity* 2009, 31, (1), 25-34; Schmidt, et al., *Proc Natl Acad Sci USA* 2009, 106, (29), 12067-72).

There are several advantages in using synthetic 5'-triphosphate RNA over 5'-triphosphate RNA generated by in vitro transcription, those include: higher purity and clearer identity of the products which are obtained reproducibly and independently from the RNA sequences used; possibilities of scale-up synthesis and introduction of theoretically all the known RNA chemical modifications (Atts, et al., *Drug Discovery Today* 2008, 13, (19-20), 842-855).

Despite these numerous applications and advantages, DNA and RNA ONTPs are difficult for access, as there is no easy and efficient method for their enzyme free, chemical synthesis. Hence, the chemical preparation of ONTPs seems to be a real challenge, since the few known recent approaches describing their synthesis on solid support (Lebedev, et al., *Nucleosides Nucleotides Nucleic Acids* 2001, 20, (4-7), 1403-9) are all associated with low efficiency, serious lack of universality in regards of the length and the sequence, difficult separation procedures resulting from low conversions, and eventually poor yields. The polyfunctional oligomeric nature of the RNA or DNA substrate, which involves the precise choice of appropriate protecting groups and overall synthetic strategy, can only be added to the existing limitations known for nucleoside triphosphate (NTP) synthesis (Burgess, et al., *Chemical Reviews* 2000, 100, (6), 2047-2059.). Moreover, as witnessed by several recent reports, synthetic efforts are still ongoing for developing a simple, efficient and universal triphosphorylation method for nucleosides (Crauste, et al., *The Journal of Organic Chemistry* 2009, 74, 9165-9172; Sun, Q et al., *Organic Letters* 2008, 10, (9), 1703-1706; Warnecke, et al., *The Journal of Organic Chemistry* 2009, 74, (8), 3024-3030).

SUMMARY

The present invention is directed to improved processes for making 5'-triphosphate oligonucleotides via a H-phosphonate intermediate. This invention embodies a method using solid-phase oligonucleotide synthesis comprising 5' H-phosphonate intermediate of a nucleotide bound to a solid-phase support. This is preferably done in the presence of diphenyl phosphite, thereby forming a hydrogenophosphonate monoester which is further oxidized and activated by a heteroaryl, and phosphorylating with a pyrophosphate. If present, the solid support may then be removed and any protecting groups, such as the 2' protecting group, may be deprotected. The improved process described herein provides a means for more efficient and economical synthesis of triphosphate oligonucleotides.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

c) pppUUGUCUCUGGUCCUUACUUAA (SEQ ID NO: 2) purified. (B) RP-LC/MS profile for pppUUGUCUCUG-GUCCUUACUUAA (SEQ ID NO: 2) purified and deconvoluted peaks list. (Table 1, Entry 11)

Figure 4A:
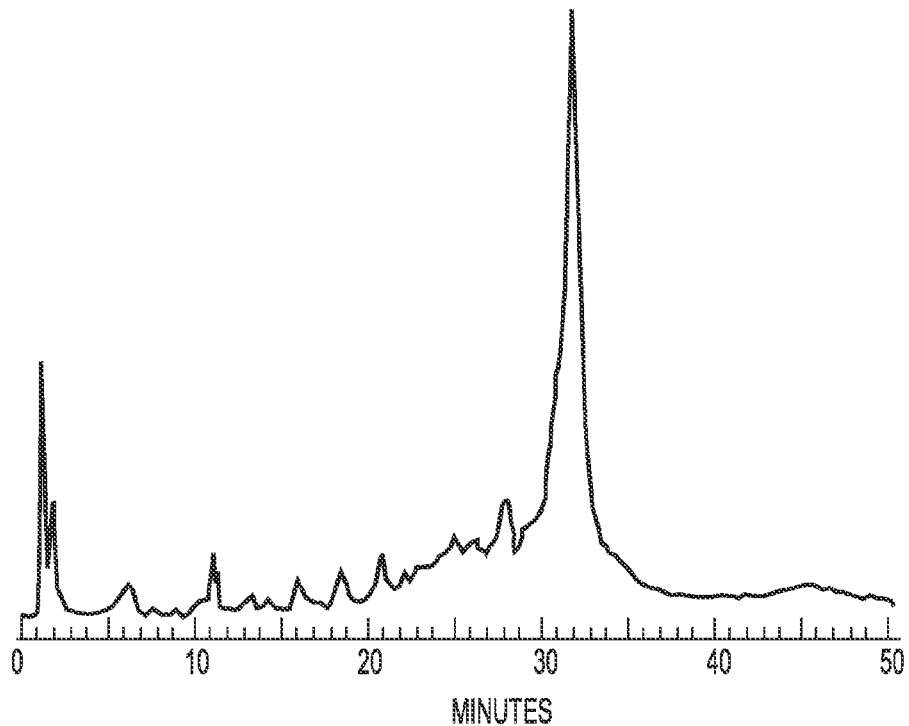
Figure 4B:
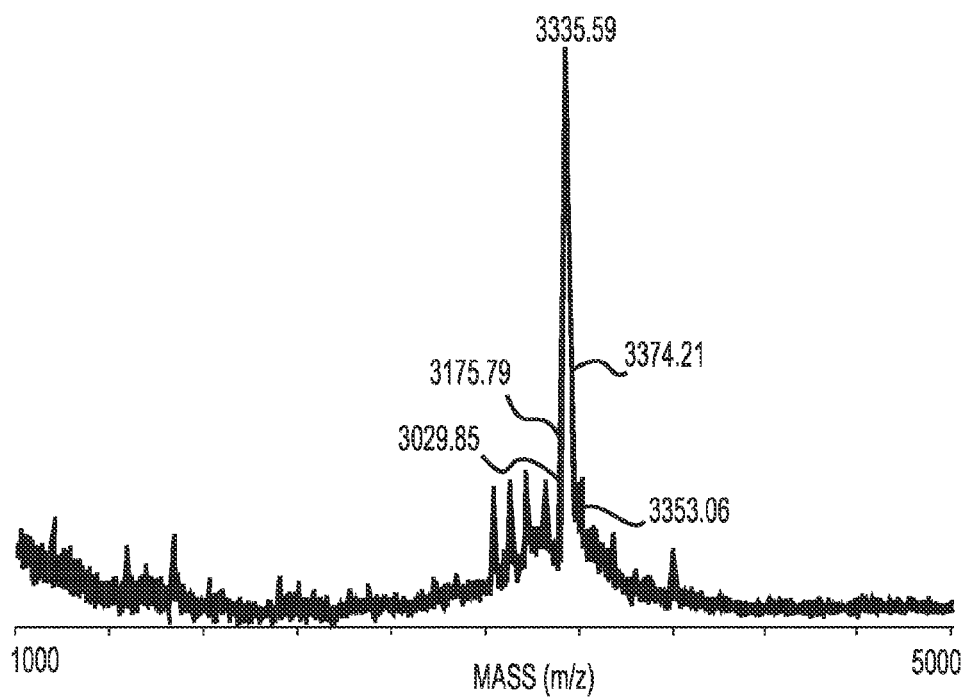

FIG. 4 (A) IE-HPLC profiles and (B) MALDI-T of MS of pppAGUUGUUCCC (SEQ ID NO: 3) (Table 1, Entry 18)

DETAILED DESCRIPTION

This invention provides a new and improved process for the preparation of oligonucleotide 5'-triphosphates (ONTPs) and for intermediates useful in this process. Utilizing said process and intermediates, oligonucleotide 5'-triphosphates are prepared from a plurality of RNA and/or DNA nucleotide subunits. The nucleotide subunits may be "natural" or "synthetic" moieties. The term "oligonucleotide" thus effectively includes naturally occurring species or synthetic species.

This invention focused on the development of a novel synthetic method for ONTPs that would be fully compatible with standard DNA and RNA synthesis on solid support. The only procedure reported so far involves the use of the Ludwig-Eckstein phosphitylation reagent (Gaur, et al., *Tetrahedron Letters* 1992, 33, (23), 3301-3304; Ludwig, et al., *The Journal of Organic Chemistry* 1989, 54, (3), 631-635). This invention uses a more stable reaction intermediate of phosphorus in the oxidation state of five.

This invention provides a highly efficient and simple method for the solid-phase synthesis of both DNA and RNA ONTPs of various length, sequence and nature. A protocol was established for providing various DNA and RNA 5'-triphosphates with high conversion, good yields and satisfactory purity of crude products, avoiding tedious chromatography purification. Most, if not all, of the steps of this preparation method use inexpensive, commercially available reagents, stable upon storage, and utilize either standard automated or simple manual experimental manipulations, which make the method useful for application in both research and industrial laboratories.

In one embodiment, oligonucleotide 5'-triphosphates of the invention can be prepared by a process comprising the steps of:

(a) synthesizing an oligonucleotide using a method selected from the group consisting of solid phase phosphoramidite, solution phase phosphoramidite, solid phase H-phosphonate, solution phase H-phosphonate, hybrid phase phosphoramidite, and hybrid phase H-phosphonate-based synthetic methods;

(b) converting the 5' hydroxyl moiety to 5'-H-phosphonate with a reagent of formula I:

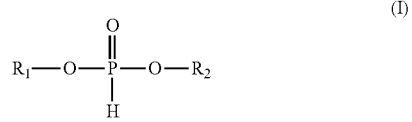

wherein $R_1$ and $R_2$ are each independently hydrogen, haloalkyl, aryl, substituted aryl, heteroaryl, substituted heteroaryl, cycloalkyl, substituted cycloalkyl, heterocycle, and substituted heterocycle, acyl, phosphoryl, substituted alkyl acyl, substituted heteroalkyl acyl, substituted aryl acyl or substituted heteroaryl acyl, substituted alkyl phosphoryl, substituted heteroalkyl acyl, substituted aryl phosphoryl or substituted heteroaryl phosphoryl; followed by an aqueous base treatment;

(c) activating the H-phosphonate of step (b) using a silylating agent, a halogenated oxidizing agent and a nitrogen containing heteroaryl;

(d) treating intermediate from step (c) with poly(alkylammonium)pyrophosphate; and (e) optionally removing the protecting group(s) and/or solid support.

In one embodiment, oligonucleotide 5'-triphosphates of the invention can be prepared by a process comprising the steps of:

(a) synthesizing an oligonucleotide using a method selected from the group consisting of solid phase phosphoramidite, solution phase phosphoramidite, solid phase H-phosphonate, solution phase H-phosphonate, hybrid phase phosphoramidite, and hybrid phase H-phosphonate-based synthetic methods;

(b) converting the 5' hydroxyl moiety to 5'-H-phosphonate with a reagent of formula II:

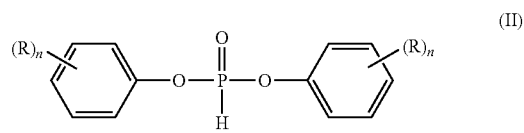

wherein R is each independently hydrogen, halogen, haloalkyl, halogen, $NO_2$, CN, acyl, and sulfonyl, aryl, substituted aryl, heteroaryl, substituted heteroaryl, cycloalkyl, substituted cycloalkyl, heterocycle, and substituted heterocycle, n is 0 to 5; followed by an aqueous base treatment;

(c) activating the H-phosphonate of step (b) using a silylating agent, a halogenated oxidizing agent and a nitrogen containing heteroaryl;

(d) treating intermediate from step (c) with poly(alkylammonium)pyrophosphate; and (e) optionally removing the protecting group(s) and/or solid support.

In one embodiment, R comprises at least one suitable EWG (electron withdrawing groups) which include halogens, $NO_2$, CN, acyl, and sulfonyl.

In one embodiment, oligonucleotide 5'-triphosphates of the invention can be prepared by a process comprising the steps of:

(a) synthesizing an oligonucleotide using a method selected from the group consisting of solid phase phosphoramidite, solution phase phosphoramidite, solid phase H-phosphonate, solution phase H-phosphonate, hybrid phase phosphoramidite, and hybrid phase H-phosphonate-based synthetic methods;

(b) converting the 5' hydroxyl moiety to 5'-H-phosphonate with diphenyl phosphite; followed by an aqueous base treatment;

(c) activating the H-phosphonate of step (b) using a silylating agent, a halogenated oxidizing agent and a nitrogen containing heteroaryl;

(d) treating intermediate from step (c) with poly(alkylammonium)pyrophosphate; and (e) optionally removing the protecting group(s) and/or solid support.

In one embodiment, step (b) is carried out in the for at least 10 minutes, 20 minutes, at least 30 minutes, at least 40 minutes, at least 50 minutes, or at least 60 minutes.

In one embodiment, the aqueous base is selected from triethyl ammonium bicarbonate, triethyl ammonium phosphate, triethyl ammonium hydrogen phosphate, triethyl ammonium sulfate, triethyl ammonium hydrogen sulfate, triethyl ammonium chloride, other ammonium aqueous buffer at pH zone 5-9, potassium carbonate, sodium carbonate, sodium bicarbonate, water.

In one embodiment, the silylating agent used in step (c) includes N,O-bis(trimethylsilyl)-acetamide (BSA), trimethylsilyl chloride; triethylsilyl chloride, trialkylsilyl chloride, triarylsilyl chloride or mixed alkyl aryl silyl chloride, Hexamethyldisilazane (HMDS)

In one embodiment, the halogenated oxidizing agent used in step (c) includes $CCl_4$ or $I_2$.

Representative examples of oxidizing agents for step (c) include: BSA and $Et_3N$ in $CCl_4$/MeCN; $I_2$ and N,O-bis(trimethylsilyl)-acetamide in MeCN/pyridine, $CCl_4$/pyridine/HMDS MeCN, and DMAP TMS-Cl in pyridine/$CCl_4$.

In one embodiment, the nitrogen containing heteroaryl is selected from the group consisting of pyridyl, substituted pyridyl, pyrimidinyl, substituted pyrimidinyl, imidazolyl, substituted imidazolyl, triazolyl, substituted triazolyl, tetrazolyl, substituted tretrazolyl, fused polyaromatic or polyheteroaromatic rings including one of the above.

In one embodiment, the poly(alkylammonium)pyrophosphate is a salt of pyrophosphate and several ammonium, pyridinium or other bulky organic-solvent soluble counterions. Examples can be selected from tris(tri-n-butylammonium)pyrophosphate, tetrakis(tri-n-butylammonium)pyrophosphate, tris(tetra-n-butylammonium)pyrophosphate, tetrakis(tetra-n-butylammonium)pyrophosphate tris(dimethylammonium)pyrophosphate, tris(tri-ethylammonium) pyrophosphate, tris(tri-isopropylammonium)pyrophosphate, tris(tri-n-propylammonium)pyrophosphate, tris(tri-t-butylammonium)pyrophosphate, tris(pyridinium)pyrophosphate, tretrakis (pyridinium)pyrophosphate, tris(diazabicyclooctyl ammonium-DABCOnium)pyrophosphate, tetrakis(DABCOnium)pyrophosphate In one embodiment, step (c) is carried out in a solvent system selected from carbon tetrachloride, 1,1-dichloroethane, chloroform, perchloroethylene, tetrachloroethylene, 1,1,2,2-tetrachloroethane, 1,1,2-trichloroethane, methylene chloride, trichloroethylene, methyl chloroform, 1,1,1-trichloroethane, 1,2,3-trichloropropane, ethylene dichloride, 1,2-dichloropropane, propylene dichloride, 1,2-dichloroethylene, acetonitrile, ethyl acetate, tetrahydrofuran (THF), dimethylsulfoxide (DMSO), dimethyl formamide (DMF), hexamethylphoshphoramide (HMPA), hexamethylphosphotriamide (HMPT), dimethylether (DME), pyridine, triethylamine, DIEA, dioxane, or combinations thereof.

In one embodiment, step (d) is carried out at room temperature for about 1 hour to about 100 hours. For example at least 10 hours, 12 hours, 15 hours, 16 hours, 17 hours, 18 hours.

In one embodiment, step (d) is carried out with microwave radiation at about 30 to about 100 degrees for at least 5 minutes, 10 minutes, 20 minutes, at least 30 minutes, at least 40 minutes, at least 50 minutes, or at least 60 minutes.

In one embodiment, the oligonucleotide obtained from step (a) comprises at least one 2' protecting group selected from alkysilyl (i.e. TBMDS),

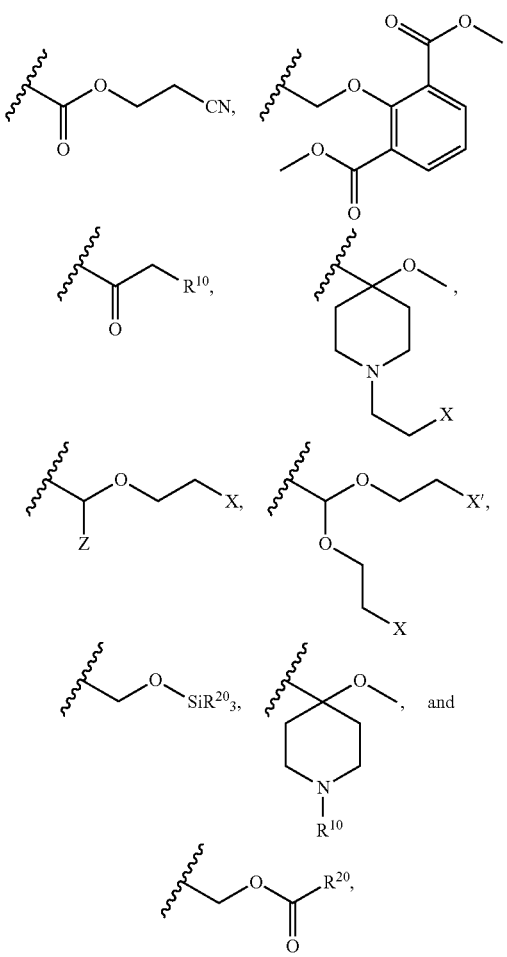

wherein X and X' are independently CN, $NO_2$, $CF_3$, F, or OMe; Z is H or alkyl; and $R^{10}$ is aryl, substituted aryl, heteroaryl or substituted heteroaryl; and $R^{20}$ is alkyl (i.e. methyl, ethyl, propyl, butyl, t-butyl, isopropyl, isobutyl).

In one embodiment, the whole process of the invention can be carried out with an automated synthesizer. In one example, steps (c) and (d) can be adapted for automated synthesis.

In another embodiment, the process of the invention can be adapted in one pot wherein purification is not necessary after each step.

In one embodiment, the 2' protected oligonucleotide 5'-triphosphates can be deprotected with a suitable deprotecting agent.

Agents for the Deprotection/Cleavage of Protecting Groups

RNA is often synthesized and purified by methodologies based on: tetrazole to activate the RNA amidite, $NH_4OH$ to remove the exocyclic amino protecting groups, n-tetrabutylammonium fluoride (TBAF) to remove the 2'-OH alkylsilyl protecting groups, and gel purification and analysis of the deprotected RNA. The RNA compounds may be formed either chemically or using enzymatic methods.

One important component of oligonucleotide synthesis is the installation and removal of protecting groups. Incomplete installation or removal of a protecting group lowers the overall yield of the synthesis and introduces impurities that are often very difficult to remove from the final product. In order to obtain a reasonable yield of a large RNA molecule (i.e., about 20 to 40 nucleotide bases), the protection of the amino functions of the bases requires either amide or substituted amide protecting groups. The amide or substituted amide protecting groups must be stable enough to survive the conditions of synthesis, and yet removable at the end of the synthesis. These requirements are met by the following amide protecting groups: benzoyl or phenoxyacetyl for adenosine, isobutyryl, acetyl, phenoxyacetyl or benzoyl for cytidine, and iso-propylphenoxyacetyl, tert-butylphenoxyacetyl or isobutyryl for guanosine. The amide protecting groups are often removed at the end of the synthesis by incubating the RNA in $NH_3$/EtOH or 40% aqueous $MeNH_2$. In the case of the phenoxyacetyl type protecting groups on guanosine and adenosine and acetyl protecting groups on cytidine, an incubation in ethanolic ammonia for 4 h at 65° C. is used to obtain complete removal of these protecting groups. However, deprotection procedures using mixtures of $NH_3$ or $MeNH_2$ are complicated by the fact that both ammonia and methylamine are corrosive gases. Therefore, handling the reagents can be dangerous, particularly when the reaction is conducted at a large scale, e.g, manufacturing scale. The volatile nature of $NH_3$ and $MeNH_2$ also requires special procedures to capture and neutralize any excess $NH_3$ and $MeNH_2$ once the deprotection reaction is complete. Therefore, the need exists for less volatile reagents that are capable of effecting the amide deprotection reaction in high yield.

One aspect of the present invention relates to amino compounds with relatively low volatility capable of effecting the amide deprotection reaction. The classes of compounds with the aforementioned desirable characteristics are listed below. In certain instances, preferred embodiments within each class of compounds are listed as well.

1) Polyamines

The polyamine compound used in the invention relates to polymers containing at least two amine functional groups, wherein the amine functional group has at least one hydrogen atom. The polymer can have a wide range of molecular weights. In certain embodiment, the polyamine compound has a molecular weight of greater than about 5000 g/mol. In other embodiments, the polyamine compound has a molecular weight of greater than about 10,000; 20,000; or 30,000 g/mol.

2) PEHA

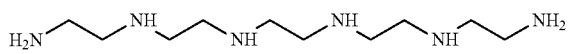

3) $PEG-NH_2$

The $PEG-NH_2$ compound used in the invention relates to polyethylene glycol polymers comprising amine functional groups, wherein the amine functional group has at least one hydrogen atom. The polymer can have a wide range of molecular weights. In certain embodiment, the $PEG-NH_2$ compound has a molecular weight of greater than about 5000 g/mol. In other embodiments, the $PEG-NH_2$ compound has a molecular weight of greater than about 10,000; 20,000; or 30,000 g/mol.

4) Short $PEG-NH_2$

The short $PEG-NH_2$ compounds used in the invention relate to polyethylene glycol polymers comprising amine functional groups, wherein the amine functional group has at least one hydrogen atom. The polymer has a relatively low molecular weight range.

5) Cycloalkylamines and Hydroxycycloalkyl Amines

The cycloalkylamines used in the invention relate to cycloalkyl compounds comprising at least one amine functional group, wherein the amine functional group has at least one hydrogen atom. The hydroxycycloalkyl amines used in the invention relate to cycloalkyl compounds comprising at least one amine functional group and at least one hydroxyl functional group, wherein the amine functional group has at least one hydrogen atom. Representative examples are listed below.

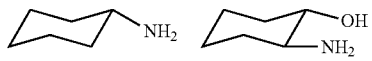

6) Hydroxyamines

The hydroxyamines used in the invention relate to alkyl, aryl, and aralkyl compounds comprising at least one amine functional group and at least one hydroxyl functional group, wherein the amine functional group has at least one hydrogen atom. Representative examples are 9-aminononanol, 4-aminophenol, and 4-hydroxybenzylamine.

7) $K_2CO_3$/MeOH with or without microwave

8) Cysteamine ($H_2NCH_2CH_2SH$) and thiolated amines

9) β-Amino-ethyl-sulfonic acid, or the sodium sulfate of β-amino-ethyl-sulfonic acid One aspect of the present invention relates to a method of removing an amide protecting group from an oligonucleotide, comprising the steps of:

admixing an oligonucleotide bearing an amide protecting group with a polyamine, PEHA, $PEG-NH_2$, Short $PEG-NH_2$, cycloalkyl amine, hydroxycycloalkyl amine, hydroxyamine, $K_2CO_3$/MeOH microwave, thioalkylamine, thiolated amine, β-amino-ethyl-sulfonic acid, or the sodium sulfate of β-amino-ethyl-sulfonic acid.

Reagents for Deprotection of a Silyl Group

As described in the previous section, the use of protecting groups is a critical component of oligonucleotide synthesis. Furthermore, the installation and removal of protecting groups must occur with high yield to minimize the introduction of impurities into the final product. The Applicants have found that the following reagents are superior for removing a silyl protecting group during the synthesis of a oligonucleotide: pyridine-HF, DMAP-HF, urea-HF, ammonia-HF, ammonium fluoride-HF, TSA-F, DAST, and polyvinyl pyridine-HF. Other aryl amine-HF reagents useful in this invention include compounds represented by A:

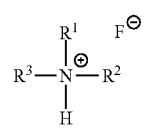

A wherein $R^1$ is alkyl, aryl, heteroaryl, aralkyl or heteroaralkyl;
$R^2$ is alkyl, aryl, heteroaryl, aralkyl or heteroaralkyl; and
$R^3$ is aryl or heteroaryl.

For example, aryl amines of the hydrofluoride salts are selected from the group consisting of (dialkyl)arylamines, (alkyl)diarylamines, (alkyl)(aralkyl)arylamines, (diaralkyl)arylamines, (dialkyl)heteroarylamines, (alkyl)diheteroarylamines, (alkyl)(heteroaryl) arylamines, (alkyl)(heteroaralkyl)arylamines, (alkyl) (aralkyl)heteroarylamines, (diaralkyl) heteroarylamines, (diheteoroaralkyl)heteroarylamines, and (aralkyl)(heteroaralkyl)heteroarylamines.

In certain instances, the rate of the deprotection reaction can be excelerated by conducting the deprotection reaction in the presence of microwave radiation. As illustrated in Example 6, the tert-butyldimethylsilyl groups on a 10-mer or 12-mer could be removed in 2 minutes or 4 minutes, respectively, by treatment with 1 M TBAF in THF, Et$_3$N-HF, or pyridine-HF/DBU in the presence of microwave radiation (300 Watts, 2450 MHz).

One aspect of the present invention relates to a method removing a silyl protecting group from a oligonucleotide, comprising the steps of:

admixing an oligonucleotide bearing a silyl protecting group with pyridine-HF, DMAP-HF, Urea-HF, TSA-F, DAST, polyvinyl pyridine-HF, or an aryl amine-HF reagent of formula A:

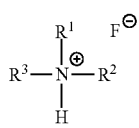

A wherein
R$^1$ is alkyl, aryl, heteroaryl, aralkyl or heteroaralkyl;
R$^2$ is alkyl, aryl, heteroaryl, aralkyl or heteroaralkyl; and
R$^3$ is aryl or heteroaryl.

In certain embodiments, the present invention relates to the aforementioned method, wherein said oligonucleotide is an oligomer of ribonucleotides.

In certain embodiments, the present invention relates to the aforementioned method, wherein the reaction is carried out in the presence of microwave radiation.

It will be recognized that oligonucleotide 5'-triphosphates having tens or even hundreds of individual nucleotide subunits can be prepared utilizing the processes and intermediates of this invention. Such very large oligonucleotide 5'-triphosphates can be assembled from smaller oligonucleotide intermediates that, in turn, would be assembled from even smaller intermediates. Thus, oligonucleotide 5'-triphosphates and oligonucleotide 5'-triphosphate intermediates of the invention contain one or more subunits.

The oligonucleotide 5'-triphosphates of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with a oligonucleotide 5'-triphosphates having a sequence that is capable of specifically hybridizing with a strand of nucleic acid coding for the undesirable protein or is capable of specifically hybridizing with a target gene thereby modulating the gene expression. Treatments of this type can be practiced on a variety of organisms ranging from unicellular prokaryotic and eukaryotic organisms to multicellular eukaryotic organisms.

In one embodiment, the preferred oligonucleotide can have all natural 2'-deoxyribo and 2'-ribonuclesides, 2'-O-methyl (2'-OMe), 2'-O-methoxyethyl (2'-MOE), 2'-deoxy-2'-ribofluoro (2'-F), 2'-deoxy-2'-arabinofluoro (2'-araF) sugar modifications and combinations there of, with and without phosphorothioate backbone at the internucleoside linkages.

In one embodiment, the preferred nucleobase modifications includes 2-ThioU, 2'-amino-A, pseudouridine, inosine, 5-Me-U, 5-Me-C, chemically modified U analogues.

In one embodiment, the preferred oligonucleotide can have ligands includes PK modulators such as lipophiles, Cholesterol and analogs, bile acids, steroids, circulation enhancers—PEG with different mol. wt. starting from 400 to up to 60,000 amu, small molecule protein binders (for e.g, naproxen or ibuprofen) and targeting ligands for receptor targeting, for e.g., folic acid, GalNAc and mannose.

Evaluation of the oligonucleotide can include incubating the modified strand (with or without its complement, but preferably annealed to its complement) with a biological system, e.g., a sample (e.g, a cell culture). The biological sample can be capable of expressing a component of the immune system. This allows identification of an oligonucleotide that has an effect on the component. In one embodiment, the step of evaluating whether the oligonucleotide modulates, e.g, stimulates or inhibits, an immune response includes evaluating expression of one or more growth factors, such as a cytokine or interleukin, or cell surface receptor protein, in a cell free, cell-based, or animal assay. Exemplary assay methods include ELISA and Western blot analysis. Growth factors that could be evaluated include TNFα, IL1α and (3, IL2, IL3, IL4, IL5, IL6, IL7, IL8, IL9, IL10, IL11, IL12, IL13, IFNα and β, and IFNγ. In preferred embodiments, a test includes evaluating expression of one or more of the interleukins IL-18, IL-1β, IL-10, IL-12, and IL-6. Relevant cell surface receptors include the toll-like receptors, e.g., TLR1, TLR2, TLR3, TLR4, TLR5, TLR6, TLR7, TLR8, or TLR9. In other preferred embodiments, a test includes evaluating expression of one or more of the toll-like receptors TL-3, TLR7, TLR8, or TLR9. Ligand interaction with TLR9 stimulates expression of NFκB. Therefore, testing whether an oligonucleotide stimulates the immune response can include assaying for NFκB protein or mRNA expression.

In one embodiment, the step of testing whether the modified oligonucleotide modulates, e.g., stimulates, an immune response includes assaying for an interaction between the oligonucleotide and a protein component of the immune system, e.g., a growth factor, such as a cytokine or interleukin, or a cell surface receptor protein. For example, the test can include assaying for an interaction between the modified oligonucleotide and a toll-like receptor, e.g., TLR1, TLR2, TLR3, TLR4, TLR5, TLR6, TLR7, TLR8, or TLR9. In one preferred embodiment, testing includes assaying for an interaction with a toll-like receptor, e.g., TLR-9. Exemplary assay methods include coimmunoprecipitation assays, bead-based co-isolation methods, nucleic acid footprint assays and colocalization experiments such as those facilitated by immunocytochemistry techniques.

Chemical modifications can include modifications to the nucleotide base, the sugar, or the backbone. In one embodiment, the oligonucleotide includes a substitution of an adenine with a 2-substituted purine (e.g., 2-amino-adenine,), a 6-substituted purine, a 7-deaza-alkyl-substituted purine, a 7-deaza-alkenyl-substituted purine, a 7-deaza-alkynyl-substituted purine, or a purine that is not adenine (e.g., guanine or inosine). In another embodiment, the candidate oligonucleotide includes a substitution of a guanine with an inosine, an aminopurine, a 2-substituted guanine, a 7-deaza-alkyl-substituted guanine, a 7-deaza-alkenyl-substituted guanine, a 7-deaza-alkynyl-substituted guanine, or an O-6-alkylated guanine. In another embodiment, the candidate oligonucleotide includes a substitution of a cytosine with a 5-substituted cytosine (e.g., a 5-methyl cytosine), an N-4 substituted cytosine, a G-clamp, an analog of a G-clamp, a 2-thio-cytosine, a 4-thio-cytosine, or a uracil. In one embodiment, the candidate oligonucleotide includes a substitution of a uracil with a 5-substituted uracil, a 4-thio-uracil, a 5-methyl-2-thiouracil, a pseudouridine, a 1-alkylpseudouridine, a 3-alkylpseudouridine or a 2-thio-uracil. In one embodiment, the oligonucleotide includes a 2'-deoxyfluoro, 2'-O-methyl, 2'-O-methoxyethyl, 2'-O-alkyl, 2'-O-alkoxyalkyl, 2'-O-allyl, 2'-O-propyl, 2'-O—(N-methyl-acetamide (NMA), 2'-O—(N,N-dimethylaminooxyethyl), or G-clamp modification. In one embodiment, the oligonucleotide includes an arabinose-containing nucleoside that replaces a ribonucleoside. In another embodiment, the arabinose-containing nucleoside can be a 2'-fluoroarabinose-containing nucleoside, or a 2'-β-methylarabinose-containing nucleoside. In another embodiment, the oligonucleotide includes a deoxynucleoside that replaces a ribonucleoside. In one embodiment, the deoxynucleoside is a 2'-fluorodeoxynucleoside, or a 2'-O-methyldeoxynucleoside.

In one embodiment, an immunoselective oligonucleotide includes at least one backbone modification, e.g., a phosphorothioate, boronaphosphate, methylphosphonate or dithioate modification. In another embodiment, the oligonucleotide includes a P-alkyl modification in the linkages between one or more of the terminal nucleotides of an oligonucleotide. In another embodiment, the sense and/or antisense strand is substantially free of stereogenic phosphorus atoms having an Rp configuration, and in another embodiment, the sense and/or antisense strand is substantially free of stereogenic phosphorus atoms having an Sp configuration.

In another embodiment, one or more terminal nucleotides of an oligonucleotide include a sugar modification, e.g., a 2' or 3' sugar modification. In one embodiment, the oligonucleotide includes at least two sugar 2' modifications. Exemplary sugar modifications include, for example, a 2'-fluoro nucleotide, a 2'-O-alkyl nucleotide, a 2'-O-alkoxyalkyl nucleotide, a 2'-O-allyl nucleotide, a 2' O-propyl nucleotide, a 2'-O-methylated nucleotide (2'-O-Me), a 2'-deoxy nucleotide, a 2'-deoxyfluoro nucleotide, a 2'-O-methoxyethyl nucleotide (2'-O-MOE), a 2'-O—N-MeAcetamide nucleotide (2'-O-NMA), a 2'-O-dimethylaminoethyloxyethyl nucleotide (2'-O-DMAEOE), a 2'-aminopropyl, a 2'-hydroxy, a 2'-arafluoro, or 3'-amidate (3'-NH in place of 3'-O), a locked nucleic acid (LNA), extended ethylene nucleic acid (ENA), hexose nucleic acid (HNA), or cyclohexene nucleic acid (CeNA).

In one embodiment, the oligonucleotide includes a methylphosphonate.

In some embodiments, the oligonucleotide includes a difluorotoluoyl (DFT) modification, e.g., 2,4-difluorotoluoyl uracil, or a guanidine to inosine substitution.

In one embodiment, the oligonucleotide includes a 5'-uridine-adenine-3' (5'-UA-3') dinucleotide wherein the uridine is a 2'-modified nucleotide, or a 5'-uridine-guanine-3' (5'-UG-3') dinucleotide, wherein the 5'-uridine is a 2'-modified nucleotide, or a 5'-cytidine-adenine-3' (5'-CA-3') dinucleotide, wherein the 5'-cytidine is a 2'-modified nucleotide, or a 5'-uridine-uridine-3' (5'-UU-3') dinucleotide, wherein the 5'-uridine is a 2'-modified nucleotide, or a 5'-cytidine-cytidine-3' (5'-CC-3') dinucleotide, wherein the 5'-cytidine is a 2'-modified nucleotide, or a 5'-cytidine-uridine-3' (5'-CU-3') dinucleotide, wherein the 5'-cytidine is a 2'-modified nucleotide, or a 5'-uridine-cytidine-3' (5'-UC-3') dinucleotide, wherein the 5'-uridine is a 2'-modified nucleotide. The chemically modified nucleotide in the oligonucleotide may be a 2'-O-methylated nucleotide. In some embodiments, the modified nucleotide can be a 2'-deoxy nucleotide, a 2'-deoxyfluoro nucleotide, a 2'-O-methoxyethyl nucleotide, a 2'-O-NMA, a 2'-DMAEOE, a 2'-aminopropyl, 2'-hydroxy, or a 2'-arafluoro, or 3'-amidate (3'-NH in place of 3'-O), a locked nucleic acid (LNA), extended nucleic acid (ENA), hexose nucleic acid (HNA), or cyclohexene nucleic acid (CeNA).

In one embodiment, the oligonucleotide has a single overhang, e.g., one end of the oligonucleotide has a 3' or 5' overhang and the other end of the oligonucleotide is a blunt end. In another embodiment, the oligonucleotide has a double overhang, e.g., both ends of the oligonucleotide have a 3' or 5' overhang, such as a dinucleotide overhang. In another embodiment, both ends of the oligonucleotide have blunt ends.

In one embodiment, the oligonucleotide includes a sense RNA strand and an antisense RNA strand, and the antisense RNA strand is 18-30 nucleotides in length. In another embodiment, the oligonucleotide includes a nucleotide overhang having 1 to 4 unpaired nucleotides, which may be at the 3'-end of the antisense RNA strand, and the nucleotide overhang may have the nucleotide sequence 5'-GC-3' or 5'-CGC-3'. The unpaired nucleotides may have at least one phosphorothioate dinucleotide linkage, and at least one of the unpaired nucleotides may be chemically modified in the 2'-position. In one embodiment, the double strand region of the candidate oligonucleotide includes phosphorothioate linkages on one or both of the sense and antisense strands. In a preferred embodiment, the candidate oligonucleotide includes phosphorothioate linkages between nucleotides 1 through 5 of the 5' or 3' end of the sense or antisense agent.

In one embodiment, the antisense RNA strand and the sense RNA strand are connected with a linker. The chemical linker may be a hexaethylene glycol linker, a poly-(oxyphosphinico-oxy-1,3-propandiol) linker, an allyl linker, or a polyethylene glycol linker. Use of a linker to connect the antisense and sense strands, will inhibit strand separation in vivo, thereby inhibiting immunostimulation.

In another embodiment, the immuno selective oligonucleotide can include at least two modifications. The modifications can differ from one another, and may be applied to different RNA strands of a double-stranded oligonucleotide. For example, the sense strand can include at least one modification, and the antisense strand can include a modification that differs from the modification or modifications on the sense strand. In another example, the sense strand can include at least two different modifications, and the antisense strand can include at least one modification that differs from the two different modifications on the sense strand. Accordingly, the sense strand can include multiple different modifications, and the antisense strand can include further multiple modifications, some of which are the same or unique from the modifications on the sense strand. For example, the process of the invention can be used to incorporate 1, 2, 3, or 4 triphosphate moiety in a double strand. In one example, a double strand oligonucleotide comprises two triphosphate moieties at the 5' end of each strand.

Using 5'-phosphoramidites it would be possible to introduce the triphosphate at the 3'-end. Here are the possible variations: 5'TP/5'TP, 5'TP/3'TP, 3'TP/5'TP or 3'TP/3'TP.

In one aspect the invention features a method of evaluating an oligonucleotide that includes providing a candidate single stranded oligonucleotide having at least one ribonucleotide modification; contacting the candidate single stranded oligonucleotide to a cell-free system, cell, or animal; and evaluating the immune response in the cell-free system, cell, or animal as compared to an immune response in a cell-free system, cell, or animal that is contacted with an unmodified single stranded oligonucleotide. The candidate single stranded oligonucleotide stimulates an immune response to a lesser or greater extent than a reference. For example, an unmodified oligonucleotide is determined to be an oligonucleotide that modulates an immune system response. In one embodiment, the candidate single-stranded oligonucleotide

DEFINITIONS

The term "linker" or "spacer" generally refers to any moiety that can be attached to an oligoribonucleotide by way of covalent or non-covalent bonding through a sugar, a base, or the backbone. The linker/spacer can be used to attach two or more nucleosides or can be attached to the 5' and/or 3' terminal nucleotide in the oligoribonucleotide. Such linker can be either a non-nucleotidic linker or a nucleotidic linker.

The term "non-nucleotidic linker" generally refers to a chemical moiety other than a nucleotidic linkage that can be attached to an oligoribonucleotide by way of covalent or non-covalent bonding. Preferably such non-nucleotidic linker is from about 2 angstroms to about 200 angstroms in length, and may be either in a cis or trans orientation, (e.g. $d(T)_n$; wherein n is 1-10 (SEQ ID NO: 4)) or non-nucleotidic (for example a linker described herein, e.g. optionally substituted alkyl, alkenyl, alkynyl, cycloalkyl, heterocyclyl or heteroaryl).

The term "nucleotidic linkage" generally refers to a chemical linkage to join two nucleosides through their sugars (e.g. 3'-3', 2'-3', 2'-5', 3'-5') consisting of a phosphate, non-phosphate, charged, or neutral group (e.g., phosphodiester, phosphorothioate, phosphorodithioate, alkylphosphonate (e.g. methylphosphonate), amide, ester, disulfide, thioether, oxime and hydrazone linkage between adjacent nucleosides.

In one embodiment, the linker/spacer between the two oligonucleotides comprises a cleavable linking group, for example a group that is potentially biodegradable by enzymes present in the organism such as nucleases and proteases or cleavable at acidic pH or under reductive conditions, such as by glutathione present at high levels intracelullarly. Some exemplary cleavable linking groups include, but are not limited to, disulfides, amides, esters, peptide linkages and phosphodiesters. Copending U.S. application Ser. No. 10/985,426, filed Nov. 9, 2004, describes cleavable tethers that are amenable for use as spacers comprising cleavable groups.

The cleavable linking group can be internal to the spacer or may be present at one or both terminal ends of the spacer. In one embodiment, the cleavable linking group is between one of the oligonucleotides and the spacer. In one embodiment, the cleavable linking group is present on both ends of the spacer. In one embodiment the cleavable linking group is internal to the spacer.

The term "halo" refers to any radical of fluorine, chlorine, bromine or iodine.

The term "aliphatic" refers to non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —N(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, azide, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

In one embodiment, the oligonucleotides of the invention is an oligonucleotide. An "iRNA agent," as used herein, is an RNA agent which can, or which can be cleaved into an RNA agent which can, stimulate or inhibit an immune response, or have no effect on an immune response. An oligonucleotide may also down regulate the expression of a target gene, preferably an endogenous or pathogen target RNA. While not wishing to be bound by theory, an oligonucleotide that down regulates expression of a target gene may act by one or more of a number of mechanisms, including post-transcriptional cleavage of a target mRNA (sometimes referred to in the art as RNAi), or pre-transcriptional or pre-translational mechanisms. An iRNA agent can include a single strand or can include more than one strands, e.g., it can be a double stranded oligonucleotide. If the oligonucleotide is a single strand it is particularly preferred that it include a 5' modification which includes one or more phosphate groups or one or more analogs of a phosphate group.

The oligonucleotides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein.

Modification described in WO 00/44895, WO01/75164, or WO02/44321 can be used herein.

The disclosure of all publications, patents, and published patent applications listed herein are hereby incorporated by reference.

Phosphate Group References.

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7, 651 and Costick et al. *Tetrahedron Lett.* 1989, 30, 4693.

Sugar Group:

Modifications to the 2' modifications can be found in Manoharan, *Biochimica et Biophysica Acta* 1489:117-130, 1999; Verma, S. et al. *Annu. Rev. Biochem.* 67:99-134, 1998 and references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310). oligonucleotide-specific chemical modifications are described in Manoharan, *Current Opinion in Chemical Biology* 8:570-579, 2004.

Methods for Identifying Oligonucleotides Having Increased Stability.

In yet another aspect, the invention relates to methods for identifying oligonucleotide having increased stability in biological tissues and fluids such as serum. oligonucleotide having increased stability have enhanced resistance to degradation, e.g., by chemicals or nucleases (particularly endonucleases) which normally degrade RNA molecules. Methods for detecting increases in nucleic acid stability are well known in the art. Any assay capable of measuring or detecting differences between a test oligonucleotide and a control oligonucleotide in any measurable physical parameter may be suitable for use in the methods of the present invention. In general, because the inhibitory effect of an oligonucleotide on a target gene activity or expression requires that the molecule remain intact, the stability of a particular oligonucleotide can be evaluated indirectly by observing or measuring a property associated with the expression of the gene. Thus, the relative stability of an oligonucleotide can be determined by observing or detecting (1) an absence or observable decrease in the level of the protein encoded by the target gene, (2) an absence or observable decrease in the level of mRNA product from the target gene, and (3) a change or loss in phenotype associated with expression of the target gene. In the context of a medical treatment, the stability of an oligonucleotide may be evaluated based on the degree of the inhibition of expression or function of the target gene, which in turn may be assessed based on a change in the disease condition of the patient, such as reduction in symptoms, remission, or a change in disease state.

In one embodiment, the method includes preparing an oligonucleotide as described above (e.g., through chemical synthesis), incubating the oligonucleotide with a biological sample, then analyzing and identifying those oligonucleotide that exhibit an increased stability as compared to a control oligonucleotide.

In an exemplified embodiment, oligonucleotide is produced in vitro by mixing/annealing complementary single-stranded RNA strands, preferably in a molar ratio of at least about 3:7, more preferably in a molar ratio of about 4:6, and most preferably in essentially equal molar amounts (e.g., a molar ratio of about 5:5). Preferably, the single-stranded RNA strands are denatured prior to mixing/annealing, and the buffer in which the mixing/annealing reaction takes place contains a salt, preferably potassium chloride. Single-stranded RNA strands may be synthesized by solid phase synthesis using, for example, an Expedite 8909 synthesizer (Applied Biosystems, Applera Deutschland GmbH, Darmstadt, Germany), as described above.

Oligonucleotide are incubated with a biological sample under the conditions sufficient or optimal for enzymatic function. After incubating with a biological sample, the stability of the oligonucleotide is analyzed by means conventional in the art, for example using RNA gel electrophoresis as exemplified herein. For example, when the sample is serum, the oligonucleotide may be incubated at a concentration of 1-10 µM, preferably 2-8 µM, more preferably 3-6 µM, and most preferably 4-5 µM. The incubation temperature is preferably between 25° C. and 45° C., more preferably between 35° C. and 40° C., and most preferably about 37° C.

The biological sample used in the incubation step may be derived from tissues, cells, biological fluids or isolates thereof. For example, the biological sample may be isolated from a subject, such as a whole organism or a subset of its tissues or cells. The biological sample may also be a component part of the subject, such as a body fluid, including but not limited to blood, serum, plasma, mucus, lymphatic fluid, synovial fluid, cerebrospinal fluid, saliva, amniotic fluid, amniotic cord blood, urine, vaginal fluid and semen. Preferably, the biological sample is a serum derived from a blood sample of a subject. The subject is preferably a mammal, more preferably a human or a mouse.

In another embodiment, the method includes selecting an oligonucleotide having increased stability by measuring the mRNA and/or protein expression levels of a target gene in a cell following introduction of the oligonucleotide. In this embodiment, an oligonucleotide of the invention inhibits expression of a target gene in a cell, and thus the method includes selecting an oligonucleotide that induces a measurable reduction in expression of a target gene as compared to a control oligonucleotide. Assays that measure gene expression by monitoring RNA and/or protein levels can be performed within about 24 hours following uptake of the oligonucleotide by the cell. For example, RNA levels can be measured by Northern blot techniques, RNAse Protection Assays, or Quality Control-PCR (QC-PCR) (including quantitative reverse transcription coupled PCR (RT-PCR)) and analogous methods known in the art. Protein levels can be assayed, for example, by Western blot techniques, flow cytometry, or reporter gene expression (e.g., expression of a fluorescent reporter protein, such as green fluorescent protein (GFP)). RNA and/or protein levels resulting from target gene expression can be measured at regular time intervals following introduction of the test oligonucleotide, and the levels are compared to those following introduction of a control oligonucleotide into cells. A control oligonucleotide can be a non-sensical oligonucleotide (i.e., an oligonucleotide having a scrambled sequence that does not target any nucleotide sequence in the subject), an oligonucleotide that can target a gene not present in the subject (e.g., a luciferase gene, when the oligonucleotide is tested in human cells), or an oligonucleotide otherwise previously shown to be ineffective at silencing the target gene. The mRNA and protein levels of the test sample and the control sample can be compared. The test oligonucleotide is selected as having increased stability when there is a measurable reduction in expression levels following absorption of the test oligonucleotide as compared to the control oligonucleotide. mRNA and protein measurements can be made using any art-recognized technique (see, e.g., Chiang, M. Y., et al., *J. Biol. Chem.* (1991) 266:18162-71; Fisher, T, et al., *Nucl. Acids Res.* (1993) 21:3857; and Chen et al., *J. Biol. Chem.* (1996) 271:28259).

Methods for Identifying Oligonucleotides with Ability to Inhibit Gene Expression.

The ability of an oligonucleotide composition of the invention to inhibit gene expression can be measured using a variety of techniques known in the art. For example, Northern blot analysis can be used to measure the presence of RNA encoding a target protein. The level of the specific mRNA produced by the target gene can be measured, e.g., using RT-PCR. Because oligonucleotide directs the sequence-specific degradation of endogenous mRNA through RNAi, the selection methods of the invention encompass any technique that is capable of detecting a measurable reduction in the target RNA. In yet another example, Western blots can be used to measure the amount of target protein present. In still another embodiment, a phenotype influenced by the amount of the protein can be detected. Techniques for performing Western blots are well known in the art (see, e.g., Chen, et al., *J. Biol. Chem.* (1996) 271:28259).

When the target gene is to be silenced by an oligonucleotide that targets a promoter sequence of the target gene, the target gene can be fused to a reporter gene, and reporter gene expression (e.g., transcription and/or translation) can be monitored. Similarly, when the target gene is to be silenced by an oligonucleotide that targets a sequence other than a promoter, a portion of the target gene (e.g., a portion including the target sequence) can be fused with a reporter gene so that the reporter gene is transcribed. By monitoring a change in the expression of the reporter gene in the presence of the oligonucleotide, it is possible to determine the effectiveness of the oligonucleotide in inhibiting the expression of the reporter gene. The expression levels of the reporter gene in the presence of the test oligonucleotide versus a control oligonucleotide are then compared. The test oligonucleotide is selected as having increased stability when there is a measurable reduction in expression levels of the reporter gene as compared to the control oligonucleotide. Examples of reporter genes useful for use in the present invention include, without limitation, those coding for luciferase, GFP, chloramphenicol acetyl transferase (CAT), β-galactosidase, and alkaline phosphatase. Suitable reporter genes are described, for example, in *Current Protocols in Molecular Biology*, John Wiley & Sons, New York (Ausubel, F. A., et al., eds., 1989); Gould, S. J., and S. Subramani, *Anal. Biochem.* (1988) 7:404-408; Gorman, C. M., et al., *Mol. Cell. Biol.* (1982) 2:1044-1051; and Selden, R., et al., *Mol. Cell. Biol.* (1986) 6:3173-3179; each of which is hereby incorporated by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

EXAMPLES

Figure 1:
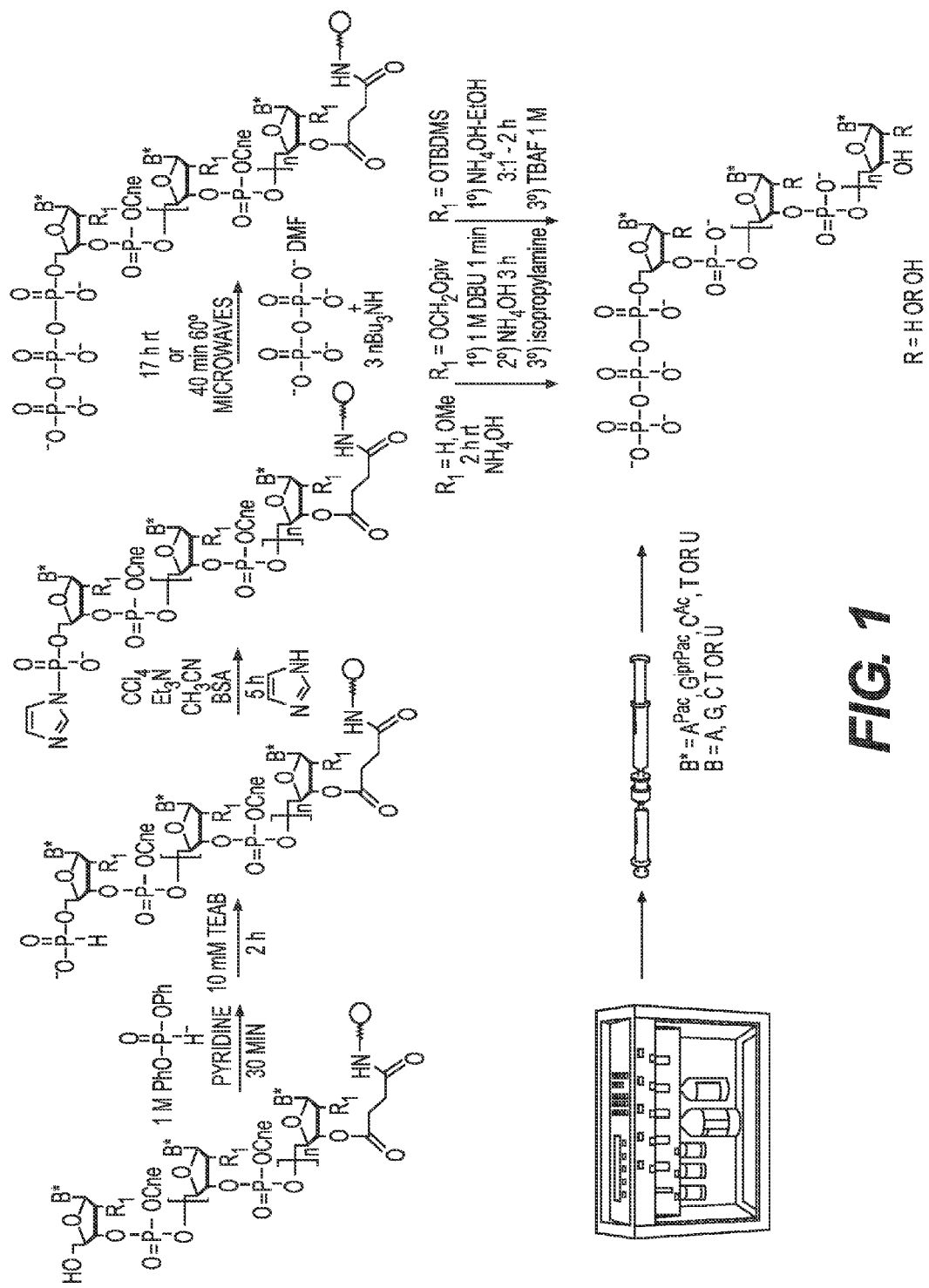
FIG. 1 is a schematic of the 5'-triphosphate synthesis

We started our study on the synthesis of DNA ONTPs, and particularly on the preparation of heptathymidinyl 5'-triphosphates (pppT$_7$), which allowed us to set the method conditions, before moving to more complex oligodeoxynucleotide substrates and eventually on RNA ONTPs. The 5'-OH T$_7$ oligonucleotides were first prepared according to the standard automated solid-supported oligonucleotide synthesis using commercial 3'-phosphoramidite thymidine and solid support (FIG. 1). They were treated with 2 M diphenyl phosphite solution in pyridine, which was manually pushed through the synthesis column yielding the corresponding 5'-H-phosphonate T$_7$ which were obtained with almost total conversion of the starting material, and still on the solid support. The 5'-triphosphate was then efficiently introduced, according to a two-step activation/phosphorylation procedure (FIG. 1). First, the H-phosphonate was oxidized with CCl$_4$ and imidazole, leading to the activated species, 5'-phosphorimidazolidate, which was further reacted with excess of 0.5 M tris(tri-n-butylammonium)pyrophosphate (TBAPP) affording the desired solid-supported pppT$_7$ with almost total conversion (FIG. 1).

Figure 2A:
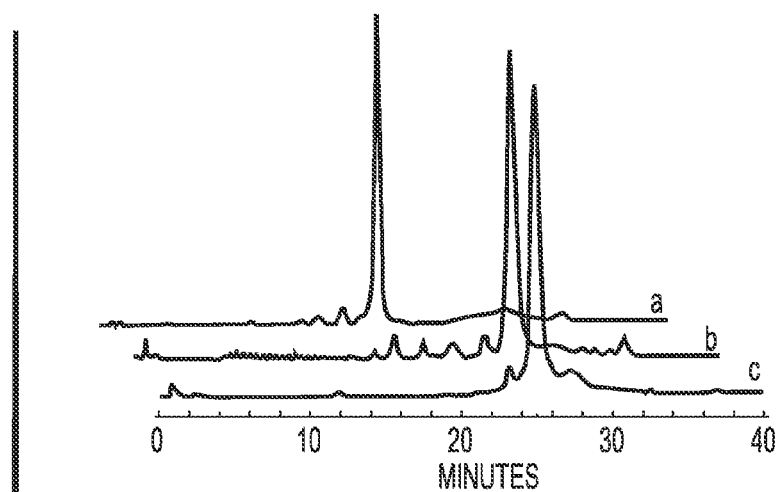
FIG. 2 (A) IE-HPLC profiles of: a) $dT_7$-5'-H-phosphonate; b) $pppdT_7$ crude; c) $pppdT_7$ purified. (B) MALDI-T of MS of: a) $dT_7$-5'-H-phosphonate; b) $pppdT_7$ crude; c) $pppdT_7$ purified (C) $^{31}P$ NMR of purified $pppdT_7$ (Table 1, Entry 2)
Figure 2B:
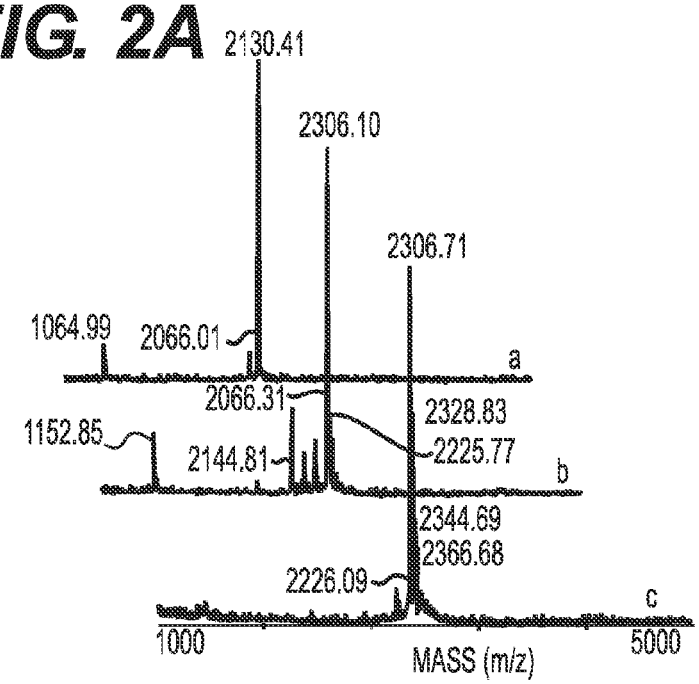
Figure 2C:
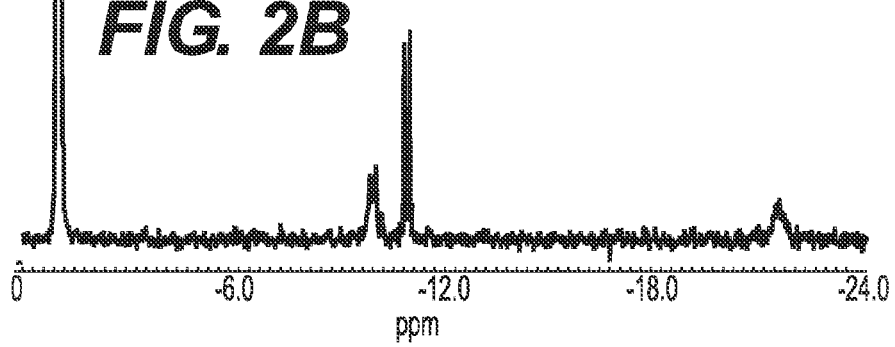

A two hour treatment with saturated aqueous ammonia at room temperature allowed removing of the oligomers from the solid support and provided the corresponding crude compounds in solution (FIG. 1 and FIG. 2). As shown on FIG. 2 A, the 5'-triphosphate oligonucleotide purity from the crude mixture was above 80% (A.b) as determined by ion exchange HPLC; and minor contamination by the non phosphorylated, H-phosphonate, mono and di phosphorylated (all below 5%) products was observed (A.b: faster eluting minor peaks as respectively listed; identity was confirmed by LC/MS analysis). The identity of the 5'-triphosphate moiety was further confirmed by MALDI-T of MS and $^{31}$P NMR analysis (FIG. 2 B and C).

Substitution of imidazole by TBAPP was investigated in details in order to establish the optimal reaction times and conditions (Table 1). For the displacement reactions performed at room temperature, we found that reaction time of 17 hours (Table 1, Entry 2) was as efficient as reaction time of 30 hours (Table 1, Entry 1). We then investigated the solid supported phosphorylation reaction upon microwave activation at 60° C. (Table 1, Entries 3 to 6). These results demonstrated that efficient phosphorylation can be achieved in only 20 minutes upon microwave activation at 60° C., showing a promising possibility of reducing reaction times without affecting the stability of the fragile 5'-triphosphate moiety. In conclusion, phosphorylation reactions performed either at room temperature for 17 hours (Entry 2), or upon microwave activation at 60° C. for 40 minutes (Entry 5) were chosen, as they provided the best results in terms of HPLC purity and recovery yields (Table 1).

Once we have demonstrated the efficiency of the method and have set the temperature/reaction time parameters, we proceeded to the synthesis of a short hetero DNA 5'-triphosphate exhibiting all the natural DNA nucleobases. Since two hours of treatment with concentrated ammonia are needed for removing the ONTP from the solid support, the fast labile protecting groups were used (i.e. acetyl for cytosine, phenoxyacetyl for adenine and iso-propyl-phenoxyacetyl for guanine) allowing efficient deprotection by this last treatment at room temperature. The hetero DNA ONTP [pppd(TCTATGT)] was obtained according to the previously developed procedure with similar results of purity and yield (Table 1, Entries 7 and 8).

As the synthesis of DNA 5'-triphosphates was successfully accomplished, we continued in increasing stepwise the complexity of the used substrates, as we moved to the synthesis of RNA 5'-triphosphates. The automated solid-supported synthesis of oligoribonucleotides is more complex if compared to the one of oligodeoxynucleotides, due to the presence of a supplementary hydroxyl group on the 2' position of the ribose, requiring an additional protection/deprotection step, deprotection being typically performed after cleavage from the solid support, as the last step of the synthesis. Hence, in order to successfully accomplish the synthesis of RNA ONTPs, this particular protection/deprotection strategy has to exhibit genuine compatibility with the presently developed phosphorylation method (FIG. 1).

The synthetic method using 2'-O-tert-butyldimethylsilyl (TBDMS) 3'-phosphoramidite building blocks is nowadays the most used strategy for the chemical synthesis of RNA (Usman, et al., *Journal of the American Chemical Society* 2002, 109, (25), 7845-7854), since these building blocks are commercially available and freely accessible. As previously, the simple 5'-triphosphate heptauridinylate (pppU$_7$), bearing seven 2'-O-TBDMS groups, was chosen as initial substrate. The 5'-triphosphate was introduced using the same experimental procedure (FIG. 1), and after cleavage form the solid support, deprotection conditions for the removal of the TBDMS groups were investigated examining the stability of the triphosphate moiety (Table 1, Entries 9 and 10). Hence, the use of the most common deprotection system involving treatment with the triethylamine 3 HF complex at 65° C. afforded only a poor yield for the pppU$_7$ oligonucleotide, due to serious decomposition (up to 35%) of the triphosphate moiety (Table 1, Entry 9). Satisfactory results, similar to those observed for DNA ONTPs, were however obtained when the 1 M tetra-n-butylammonium fluoride (TBAF) reagent was used at room temperature for 20 hours (Table 1, Entry 10). This deprotection procedure did not affect the integrity of the triphosphate group. However, the tedious desalting procedures needed for efficient removal of excess TBAF led to significantly lower yields for the U$_7$ ONTP, compared to those for DNA ONTPs (Table 1). Nevertheless, this whole method efficiently provided RNA ONTPs with satisfactory purity (74.6%) of the crude mixtures, and somewhat lower, but still satisfactory recovery (Table 1, Entry 10).

TABLE 1

| Entry | ONTP sequence[a] | Synthesis Conditions[b,c,d] | Scale (μmol) | HPLC purity (%)[e,f,g] | OD$_{260}$ | MS[h,i] (negative mode) |
|---|---|---|---|---|---|---|
| 1 | pppdT$_7$ | 30 h at rt[b] | 0.5 | 82.5[e] | 22.2 | Calcd: 2306.35, Found[h]: 2306.66 |

TABLE 1-continued

| Entry | ONTP sequence[a] | Synthesis Conditions[b,c,d] | Scale (µmol) | HPLC purity (%)[e,f,g] | $OD_{260}$ | MS[h,i] (negative mode) |
|---|---|---|---|---|---|---|
| 2 | pppdT$_7$ | 17 h at rt[b] | 0.5 | 83.8[e] | 18.0 | Calcd: 2306.35, Found[h]: 2306.10 |
| 3 | pppdT$_7$ | 2 h MW at 60° C.[b] | 0.25 | 81.9[e] | 9.0 | Calcd: 2306.35, Found[h]: 2306.67 |
| 4 | pppdT$_7$ | 1 h MW at 60° C.[b] | 0.25 | 81.5[e] | 7.5 | Calcd: 2306.35, Found[h]: 2306.99 |
| 5 | pppdT$_7$ | 40 min MW at 60° C.[b] | 0.5 | 83.4[e] | 20.0 | Calcd: 2306.35, Found[h]: 2306.82 |
| 6 | pppdT$_7$ | 20 min MW at 60° C.[b] | 0.5 | 80.5[e] | 24.0 | Calcd: 2306.35, Found[h]: 2306.93 |
| 7 | pppd(TCTATGT) | 17 h at rt[b] | 0.5 | 83.8[e] | 28.0 | Calcd: 2325.36, Found[h]: 2325.70 |
| 8 | pppd(TCTATGT) | 40 min MW at 60° C.[b] | 0.5 | 82.6[e] | 25.0 | Calcd: 2325.36, Found[h]: 2325.48 |
| 9 | pppU$_7$ | TBDMS[c]; 40 min MW at 60° C.[b]; Et$_3$N–3HF[d] | 0.25 | 57.8[e] | n.d. | Calcd: 2320.17, Found[h]: 2320.51 |
| 10 | pppU$_7$ | TBDMS[c]; 40 min MW at 60° C.[b]; TBAF[d] | 0.25 | 74.6[e] | 4.2 | Calcd: 2320.17, Found[h]: 2320.05 |
| 11 | pppUUGUCUCUGGUCCUUACUUAA (SEQ ID NO: 2) | TBDMS[c]; 17 h at rt[b], TBAF[d] | 2.0 | 73.8[f] | 154.0 | Calcd: 6787.87, Found[i]: 6787.17 |
| 12 | pppUUGUCUCUGGUCCUUACUUAA (SEQ ID NO: 2) | TBDMS[c]; 17 h at rt[b], TBAF[d] | 10.0 | N.A.[f] | N.A. | Calcd: 6787.87, Found: N.A. |
| 13 | pppAAGUAAGGACCAGAGACAAdTsdT (SEQ ID NO: 5) | TBDMS[c]; 17 h at rt[b], TBAF[d] | 4.0 | N.A.[f] | N.A. | N.A. |
| 14 | pppAccGAAGuGuuuGuccdTsdT (SEQ ID NO: 6) | TBDMS[c]; 17 h at rt[b], TBAF[d] | 0.25 | 67.5[e] | 25.0 | Calcd: 7033.35, Found[i]: 7032.31 |
| 15 | pppaaguaaggaccagagacaadTsdT (SEQ ID NO: 7) | 17 h at rt[b] | 4.0 | 87.0[g] | 300.0 | Calcd: 7307.84, Found[i]: 7305.71 |
| 16 | pppU$_7$ | PivOM approach[c]: 40 min MW at 60° C.[b]; 10% piperidine[d] | 0.25 | 77.3[e] | 11.5 | Calcd: 2320.17, Found[h]: 2320.47 |
| 17 | pppU$_7$ | PivOM approach[c]: 40 min MW at 60° C.[b]; 1M DBU[d] | 0.25 | 76.9[e] | 9.1 | Calcd: 2320.17, Found[h]: 2320.85 |

TABLE 1-continued

| Entry | ONTP sequence[a] | Synthesis Conditions[b, c, d] | Scale (μmol) | HPLC purity (%)[e, f, g] | OD$_{260}$ | MS[h, i] (negative mode) |
|---|---|---|---|---|---|---|
| 18 | pppAGUUGUUCCC (SEQ ID NO: 3) | PivOM approach[c]; 17 h at rt[b]; 1M DBU[d] | 0.5 | 77.2[e] | 24.0 | Calcd: 3336.84, Found[h]: 3335.59 |

[a] d = 2'deoxy; Upper case = 2'OH; Lower case = 2'-O-Me; s = phosphorothioate; ppp = 5'-triphosphate.
[b] Phosphorylation conditions.
[c] 2'-Protecting group RNA synthesis approach.
[d] Deprotection conditions for 2'-O-TBDMS protecting groups or the backbone 2-cyanoethyl groups.
[e] Ion-exchange HPLC gradient 0 to 0.5M NaCl in 40 min.
[f] Ion-exchange HPLC gradient 0 to 0.7M in 40 min.
[g] Reverse-phase HPLC gradient 0 to 50% CH$_3$CN in 15 min.
[h] MALDI-Tof MS using THAP-citrate matrix.
[i] ESI MS using RP-LC/MS.

Figure 3A:
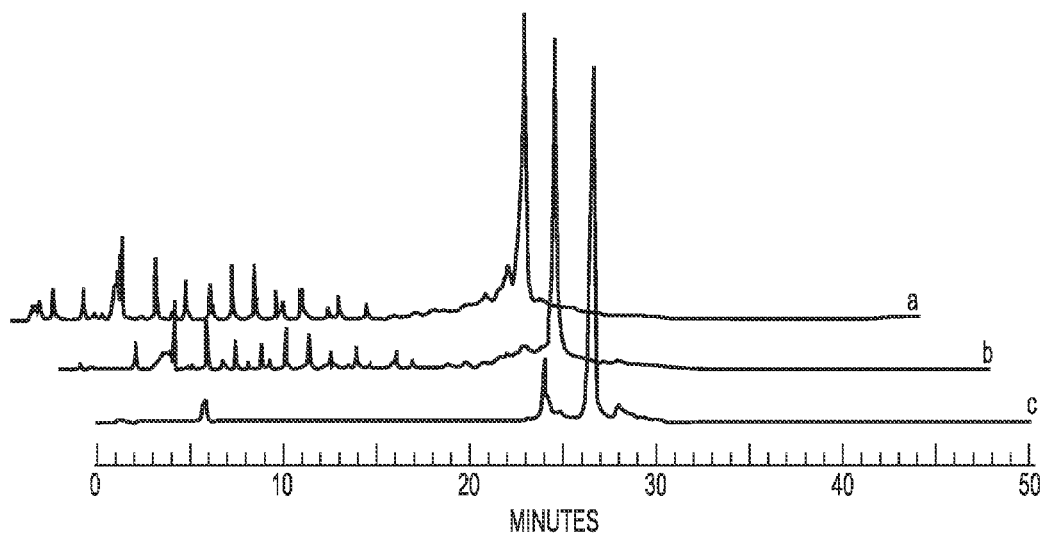
FIG. 3 (A) IE-HPLC profiles of: a) UUGUCUCUGGUC-CUUACUUAA-5'-H-phosphonate (SEQ ID NO: 1); b) ppp-UUGUCUCUGGUCCUUACUUAA (SEQ ID NO: 2) crude.
Figure 3B:
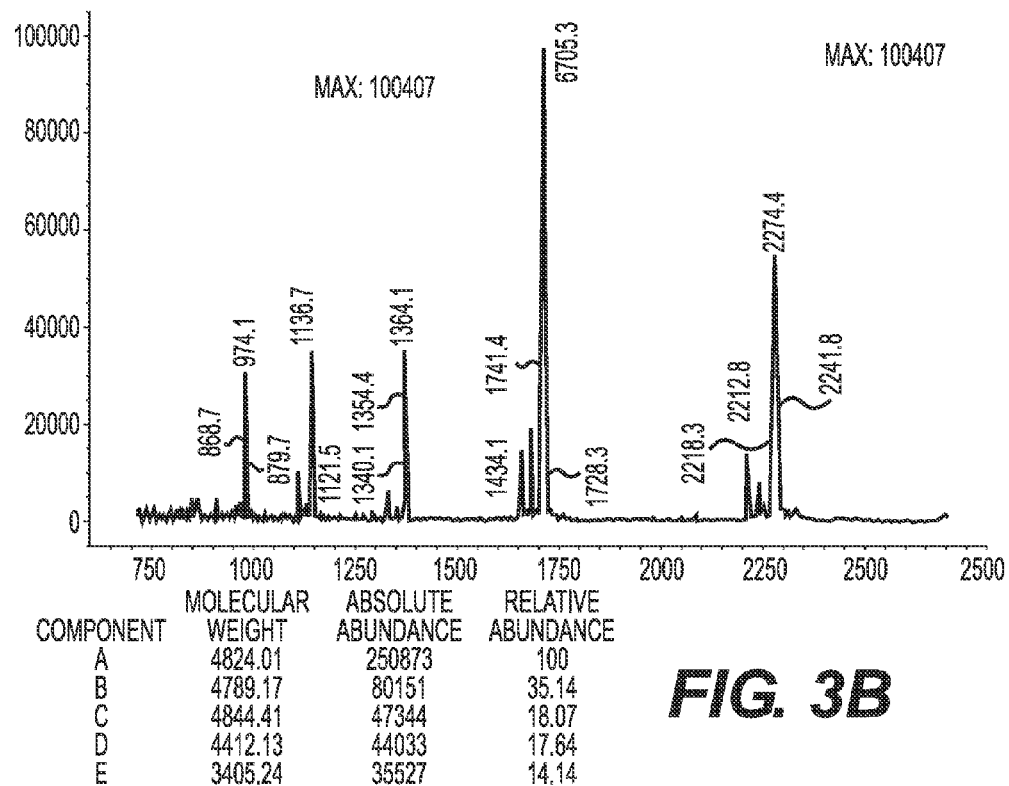

We next concentrated on the synthesis of several 21-mer hetero RNA 5'-triphosphates using the 2'-O-TBDMS protection, but also on the synthesis of chimerical substrates composed of alternated 2'-O-methyl/2'-O-TBDMS, as well as fully 2'-β-methyl substituted substrates, some of them exhibiting a phosphorothioate internucleotide linkage (Table 1, Entries 11 to 15). It is worth stressing on the fact that the possibility of synthesizing chemically modified 5'-triphosphate RNA represents a great advantage to the enzymatic methods of synthesis, and that, on the other hand, their efficient chemical synthesis is a real challenge. In addition, there are several obvious difficulties about the efficient synthesis of the starting 21-mer RNA molecules, the straightforward characterization of the long oligomer products and their safe handling and storage. Despite these drawbacks, we smoothly applied our method for solid-phase 5'-triphosphate synthesis (Table 1, Entries 11 to 15 and FIG. 3), obtaining acceptable purity of the crude RNA 5'-triphosphate compounds (about 80% of the mixtures), after deblocking the RNA from the solid support with concomitant removal of the fast labile base protecting groups, using a mixture of saturated ammonia and ethanol (Wu, et al., *Nucl. Acids Res.* 1989, 17, (9), 3501-3517.) at room temperature (FIG. 1), followed by TBAF treatment for the removal of all TBDMS groups, as established for pppU$_7$. Simple desalting procedure provided comfortable quantity of recovered product (Table 1), slightly contaminated by run-off and/or chain cleavage products (FIG. 3A.b), which were easily removed after purification of the crude material by preparative chromatography (FIG. 3A.c; see FIGS. 5-14). However, chromatographic purification provided a significant loss of amount for the target compound (e.g. 154 OD$_{260}$ before purification Vs. 45 OD$_{260}$ after, for Entry 11, Table 1; see Supporting Information for details) and some minor degradation of the RNA 5'-triphosphate (FIG. 3A.c).

The identity of the 5'-triphosphate product was further confirmed by MS (FIGS. 3B.b and 3B.c) NMR, exhibiting as well some minor contamination by the reaction hydrolysis and/or decomposition by-products (i.e. the non phosphorylated, H-phosphonate, mono and di phosphorylated products), as it was previously observed for the synthesis of pppT$_7$ (FIG. 2).

Those by-products could not be significantly removed from the mixture after chromatography purification (FIG. 3B.c), but their minor presence should eventually be tolerable, since they usually do not alter with the biological activity of the triphosphate products (Schlee, et al. *Immunity* 2009, 31, (1), 25-34). Hence, we successfully synthesized 4 different 21-mer RNA sequences (Table 1): a purine-rich (Entry 11), a pyrimidine-rich (Entry 13), a 2'-OH/2'-O-methyl chimera (Entry 14) and a full 2'-O-methyl one (Entry 15). We also successfully scaled-up the initial small scale experiments, as we used quantities from 0.25 to 10 μmol with similar success, affording up to several milligrams of RNA 5'-triphosphate and showing that the synthetic method can provide smaller and greater quantities of target ONTP with equal efficiency.

Prior to this work, the base labile 2'-O-pivaloyloxymethyl (PivOM) group was developed in our group as efficient protecting group for RNA synthesis (Layergne, T.; Bertrand, J. R.; Vasseur, J. J.; Debart, F., A Base-Labile Group for 2'-OH Protection of Ribonucleosides: A Major Challenge for RNA Synthesis. *Chemistry-a European Journal* 2008, 14, (30), 9135-9138) and in WO2009/144418 A1, (PCT/FR2009/000624 filed May 28, 2009) which are hereby incorporated by reference by their entirety. This has been the first reported 2'-protecting group for RNA synthesis that can be efficiently removed by the above mentioned room temperature treatment with concentrated ammonia, removing the nucleobase protecting groups and simultaneously releasing the oligonucleotide from the solid support. In comparison to the standard TBDMS protection approach, this synthetic procedure involves shorter deprotection times, and above all, greatly simplifies the work-up by avoiding tedious desalting procedure or chromatography purification, leading to higher isolated yields for synthetic RNA in much shorter times. We took advantage of this strategy, in order to simplify the method for synthesis of RNA ONTPs and increase the yields of recovered material. Using the 2'-O-PivOM-3'-phosphoramidite uridine building block, we first successfully prepared U$_7$ ONTPs, performing the phosphorylation reaction at both room temperature and upon microwave activation, as previously established (Table 1). As reported,[25] a first non-nucleophilic basic treatment prior the ammonia treatment is required for the removal of the cyanoethyl protections of all the internucleosidic phosphate groups avoiding the chain breakage. We first investigated the use of a 10% piperidine solution in dry acetonitrile (Table 1, Entry 16), but we observed that some undesirable 5'-phosphoropiperidinate adducts (up to 10%) were formed after displacement of pyrophosphate from the triphosphate moiety by piperidine. Secondly, a treatment using non nucleophilic DBU 1 M solution in dry acetonitrile gave a clean elimination of cyanoethyl groups, without any substitution or hydrolysis reactions on the triphosphate group (Table 1, Entry 17). As expected, when using the 2'-O-PivOM approach, we recovered more than twice as much material compared to the U$_7$ ONTP prepared using the TBDMS approach (Table 1, Entry 10). This result demonstrated that the recently developed 2'-O-PivOM approach for RNA synthesis finds particular interest when applied for the synthesis of RNA ONTPs, as pppU$_7$ were prepared with shorter reaction times, with more convenient manipulations and obtained with higher yields. In order to confirm this on a hetero RNA substrate, we successfully applied this protocol for the synthesis of the short hetero RNA pppAGUUGUUCCC (SEQ ID NO: 3) (Table 1, entry 18). This particular RNA 5'-triphosphate sequence was chosen since it is particularly important as a precursor for the 5'-cap structure of flaviviruses and is particularly difficult of access. The 10-mer RNA ONTP was successfully prepared providing high yield and good purity of the crude product (Table 1, Entry 18 and FIG. 4). The synthesis of longer RNA 5'-triphosphates using the PivOM approach are currently in progress.

Representative Triphosphate Synthesis

The Scheme of the TP synthesis using the H-Phosphonate oxidation approach:

Scheme 1: Solid phase synthesis of oligonucleotide 5' triphospahtes using the H-phosphonate oxidation approach

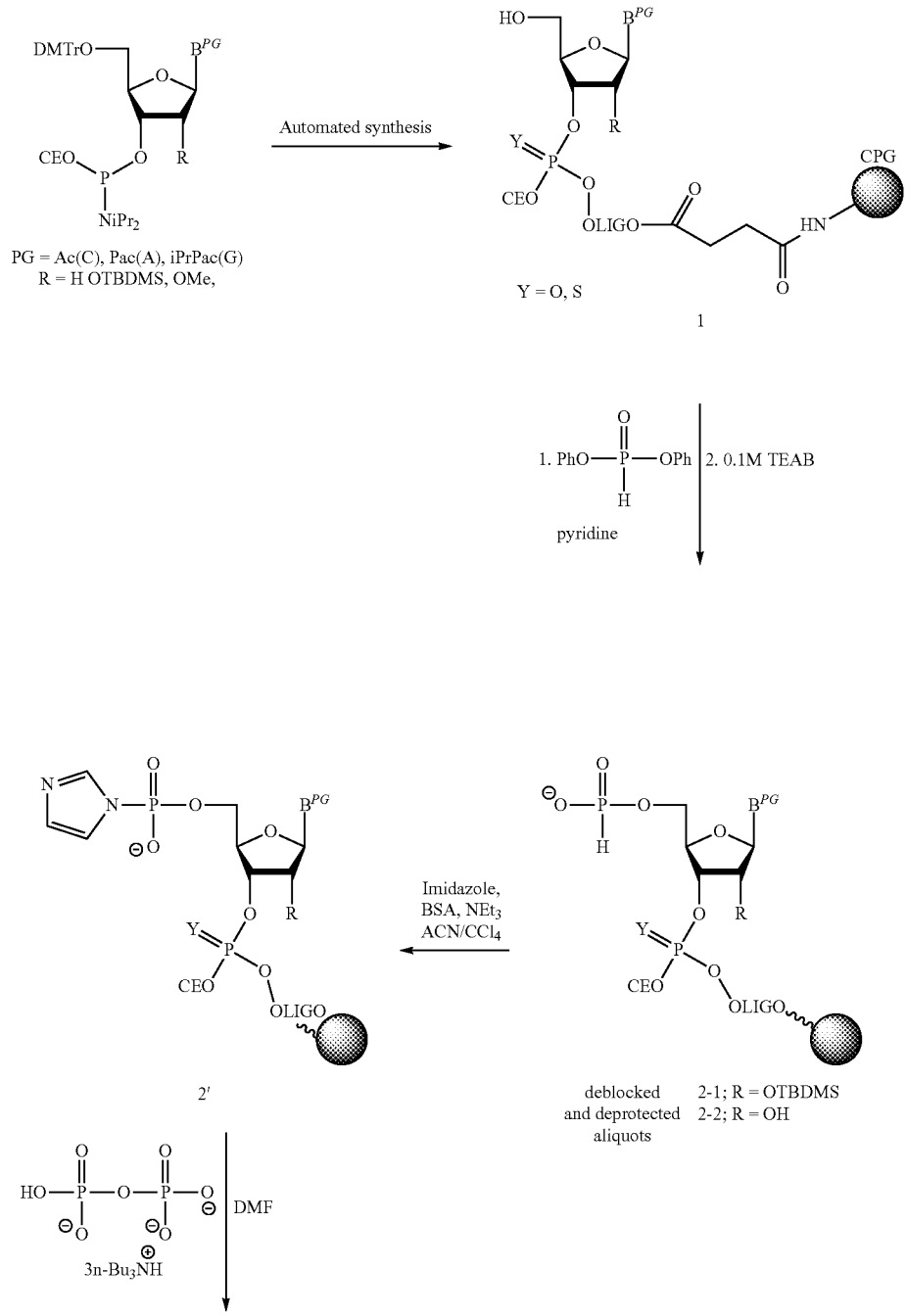

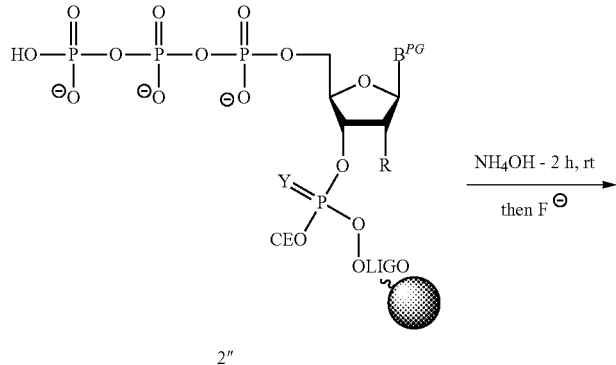

2″

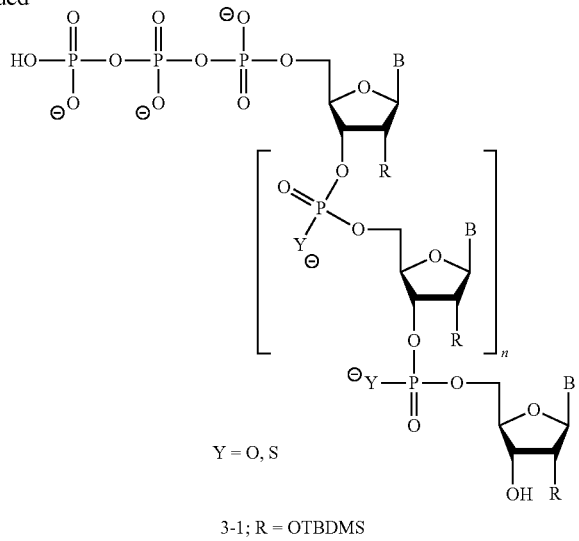

Y = O, S 3-1; R = OTBDMS
3-2; R = OH

Used Oligos (1):
1a: dT$_{10}$ (SEQ ID NO: 8)
1b: aac gaa gug uug uuu guc cdTsdT (SEQ ID NO: 9) (lower case = 2′OMe; s = phosphorothioate); target KSP, sense strand
1c: Acc GAA GuG uuG uuu Guc cdTsdT (SEQ ID NO: 10) (upper case = 2′OTBDMS); target KSP, sense strand
1e: UUGUCUCUGGUCCUUACUUAA (SEQ ID NO: 11) (upper case = 2′OTBDMS); target PTEN, antisense strand Experimental 1. Oligonucleotide Synthesis.

Oligonucleotides 1 a-c were synthesized on CPG solid support (Glen Research) using standard automated oligonucleotide synthesis on an ABI394 (Applied Biosystems) synthesizer on the 40 umol scale. Standard synthesis cycle was used for detritylation, phosphoramidite coupling, oxidation (sulfurization) and capping steps. 3′-di-isopropylphosphoramidites bearing fast labile nucleobase protecting groups (i.e. Ac for C, Pac for A, iPrPac for G) were commercially available (Chem Genes), and used as a 0.2 M solution in anhydrous acetonitrile (Glen). Capping A reagent was a Pac$_2$O solution. A Trityl Off synthesis was performed as the last DMTr group was removed at the end of the synthesis. The oligonucleotide was washed with anhydrous acetonitrile and reverse flushed with argon. The solid supported oligonucleotide was then stocked at −20° C.

2. Synthesis of Oligonucleotide 5′-H-Phosphonate Monoesters 2:

0.25 to 2 umol of solid supported oligonucleotide 1 (10 to 50 mg) was placed in a dry Twist oligonucleotide synthesis column (Glen). The column was closed and flushed with argon. A 1 M pyridine solution of diphenyl phosphite (mixture of 0.4 mL of diphenyl phosphite, Aldrich and 1.6 mL of anhydrous pyridine, Aldrich) was gently pushed through the synthetic column back and forth for 30 minutes at room temperature. The column was then emptied, washed thoroughly with acetonitrile and reverse flushed with argon. 100 mM aqueous TEAB (Aldrich) was then pushed through the column for 2 hours. The column was then emptied, washed with anhydrous acetonitrile and reverse flushed with argon. It was then placed under vacuum over P$_2$O$_5$ for 24 hours, and then stocked at −20° C.

2 can be deprotected using aqueous ammonia (JTBaker)/ethanol—3:1 (v/v) for 2 hours at room temperature (2-1), and then 1 M TBAF (Aldrich) treatment for 24 hours at room temperature, desalting and purification (2-2).

3. Oxidation of Solid Supported H-Phosphonates 2:

Solid supported H-Phosphonates 2 (0.25 to 2 umol) were placed in an empty Twist synthesis column. 5 to 6 beads of activated 4 A molecular sieves were introduced inside the column. The column was closed and flushed with argon. The oxidation solution was then prepared as follows: 150 mg (2 mmol) of imidazole (Aldrich) were coevaporated twice with anhydrous acetonitrile and then dried under vacuum over P$_2$O$_5$. The residue was then redissolved in anhydrous acetonitrile (0.8 mL), anhydrous CCl$_4$ (Aldrich, 0.8 mL), anhydrous triethylamine (Sigma, 0.1 mL) and N,O-bis-trimethylsilyl acetamide (Aldrich, 0.4 mL). The resulting solution was dried over activated 4A molecular sieves for 10 min, and then degassed with Argon for 30 seconds; it was then pushed gently through the column for 5 hours at room temperature. The column was emptied and washed quickly twice with methanol, then reverse flushed with argon.

4. Phosphorylation of Solid Supported Phosphorimidazolidates 2′:

1 mL of 0.5 M tris-tributylammonium pyrophosphate (Aldrich, 1 g in 2 mL of anhydrous DMF, Aldrich; dried over activated molecular sieves for 24 h at 4° C.) was pushed through the synthesis column for 30 h. The column was then emptied, washed several times with methanol and acetonitrile, followed by reverse flush with argon.

5. Deprotection of Solid Supported Oligonucleotide Triphosphates 2″:

The dried solid support CPG carrying the oligonucleotide triphosphates 2″ was transferred from the Twist column to an empty screw cap plastic vial (10 mL). 2 mL of 30% NH$_4$OH (JTBaker)/ethanol—3:1 (v/v) were added and left to react for 2 hours at room temperature. The solution was decanted, evaporated and then lyophilized from water, affording partly or fully deprotected oligonucleotide triphosphates 3-1. Further deprotection of the 2' silyl groups was performed as follows: lyophilized 3-1 was placed in plastic vial and dissolved in 0.5 mL of 1 M TBAF (Aldrich, THF solution). The solution was left to react for 24 hours at room temperature. It was then diluted with 2 mL of water and applied on an equilibrated illustra NAP-25 desalting column (GE Healthcare). It was then eluted with 3.5 mL of water. The solution was collected and lyophilized, affording fully deprotected oligonucleotide triphosphate 3-2.

Further purification—Ion exchange semi-preparative chromatography, followed by semi preparative reverse phase desalting was performed on AKTA purifying system for compound 3.2.e. Conditions were: IE-HPLC semi prep:column: Dionex DNA; gradient (buffer A: 25 mM TRIZMA HCl-Aldrich; buffer B: 25 mM TRIZMA HCl 1 M NH$_4$Cl-Aldrich; 0 to 0.7 M NH$_4$Cl in 5 CV; flow 10 mL/min). RP-HPLC semi prep:column:C18; gradient (buffer A: 25 mM TEAB-Aldrich; buffer B: Acetonitrile-E. Merck; 0 to 50% acetonitrile in 5 CV; flow 10 mL/min). Collected desalted fraction was freezed and lyophilized, then stored at −20° C.

6. Results:

Appropriate oligonucleotides were analyzed by ion exchange HPLC using a gradient of 0 to 0.5 M NaCl (10 mM TRIZMA) in 40 min on a Dionex BioLC DNA Pac PA100 column, installed on a Waters apparatus. Samples were injected on a 25 OD per mL concentration, injecting 10 uL. Data were processed using the Empower 2 software. Molecular weight of the appropriate compounds was determined after an LC/MS analysis on a RP LC-Q-T of mass spectrometer (Applied Biosystems). Ion deconvolution was applied for determination of the molecular weight.

Control (Aliqoute) of 5'-H-Phosphonate Monoester (2):

| HPh-Sequence | Calctd MW | 2-1 - TBDMS-On Found MW (abundance) | 2-2 - TBDMS-Off Found MW (abundance) | 2-2 IE HPLC* Rt min (area) |
|---|---|---|---|---|
| a | 3043.00 | — | 3042.89 (100) | 27.49$^a$ (>90%) |
| b | 6970.61 | — | 6968.81 (100) 6904.72** (28.8) | 38.55$^a$ (>80%) |
| c | 2-1 - 7772.51 2-2 - 6858.39 | 7770.43 (100) | 6857.01 (100) | 39.81$^a$ (>80%) |
| e | 2-1 - 9012.47 2-2 - 6612.9 | n.d. | 6611.58 (100) 6633.75 (Na, 40) | 28.24$^b$ (>68%) |

*gradient:
$^a$ 0 to 0.5M NaCl (10 mM TRIZMA) in 40 min; Dionex BioLC DNA Pac PA100 column
$^b$ 0 to 0.7M NaCl (10 mM TRIZMA) in 40 min; Dionex BioLC DNA Pac PA100 column
**starting 5'OH oligo (1)

Target 5'-Triphosphates (3):

| TP-Sequence | Calctd MW | 3-1 - TBDMS-On Found MW (Adduct, abundance) | 3-2 - TBDMS-Off Found MW (Adduct, abundance) | 3-2 IE HPLC* Rt min (area) | OD$_{260}$ |
|---|---|---|---|---|---|
| a | 3219.96 | — | 3256.79 (K, 100) 3218.85 (48) 3138.82***(27) 3240.93 (Na, 16) | 28.65$^a$ (>70%) DP at 28.47$^a$ (10%) | 45 OD from 0.5 umol |
| b | 7146.57 | — | 7182.90 (K, 100) 6904.68** (55) 7204.46 (K, Na, 30) 7144.38 (25) 7166.78 (Na, 21) 7064.61*** (19) | 37.52$^a$ (>90%) | 25 OD from 0.25 umol |
| c | 3-1 - 7948.47 3-2 - 7034.35 | 7984.37 (K, 100) 7868.89*** (37) | 7053.35 (Na, 100) 7070.73 (K, 66) | 39.81$^a$ (>80%) | 25 OD from 0.25 umol |
| e | 3-1 - 9188.42 3-2 - 6788.87 | 8966.05 (K, −2 TBDMS, 100) 8882.09 (K, −1 TBDMS, 50) | 6826.08 (K, 100) 6787.81 (40) 6847.95 (K, Na, 28) 6810.11 (Na, 23) | 26.63$^b$ (>73.4% crude; 86.4% pure) | 154 OD from 2.0 umol |

*gradient:
$^a$ 0 to 0.5M NaCl (10 mM TRIZMA) in 40 min; Dionex BioLC DNA Pac PA100 column
$^b$ 0 to 0.7 M NaCl (10 mM TRIZMA) in 40 min; Dionex BioLC DNA Pac PA100 column
**starting 5'OH oligo (1)
***5' diphosphate Oligonucleotide Triphosphate and Diphosphate Synthesis. Diphosphates. Annealing and production of dsRNAi TPs

1. Synthesis of PTEN 21 Mer Oligonucleotides RNAs (Antisense Strand) on Solid Support CPG:

1d: uUfgUfcUfcUfgGfuCfcUfuAfcUfuAfa (SEQ ID NO 12) (lower case = 2'OMe, upper case f = 2'Fluoro)

1f: uUgUcUcUgGuCcUuAcUuAa (SEQ ID NO: 13) (upper case = 2'OTBDMS, lower case = 2'OMe)

1e: UUGUCUCUGGUCCUUACUUAA (SEQ ID NO: 14) (upper case = 2'OTBDMS); target PTEN, antisense strand -continued 1g: AAGUAAGGACCAGAGACAAdTsdT (SEQ ID NO: 15)
(upper case = 2'OTBDMS, s = phosphorothioate);
target PTEN, sense strand 1h: aaguaaggaccagagacaadTsdT (SEQ ID NO: 16)
(lower case = 2'OMe, s = phosphorothioate);
target PTEN, sense strand Oligonucleotides 1d-h were synthesized on CPG solid support (Glen Research) using standard automated oligonucleotide synthesis on an ABI394 (Applied Biosystems) synthesizer on the 40 umol scale. Standard synthesis cycle was used for detritylation, phosphoramidite coupling, oxidation (sulfurization) and capping steps. 3'-di-isopropylphosphoramidites bearing fast labile nucleobase protecting groups (i.e. Ac for C, Pac for A, iPrPac for G) were commercially available (Chem Genes), and used as a 0.2 M solution in anhydrous acetonitrile (Glen). Capping A reagent was a $Pac_2O$ solution. A Trityl Off synthesis was performed as the last DMTr group was removed at the end of the synthesis. The oligonucleotide was washed with anhydrous acetonitrile and reverse flushed with argon. The solid supported oligonucleotide was then stocked at $-20°$ C.

Oligonucleotide synthesis of 1d was in progress, pending delivery of custom synthesized 2'Fluoro 3' phosphoramidites of G and A, bearing the fast labile protecting groups (iPrPac and Pac, respectively). It was synthesized in a similar fashion as previously described for oligonucleotides 1a-c and 1e-f.

2. Synthesis of Oligonucleotide 5' Triphosphates and Diphosphates:

Scheme 2: Solid phase synthesis of oligonucleotide 5' triphospahtes (n = 1) and 5' diphosphates (n = 0) using the H-phosphonate oxidation approach

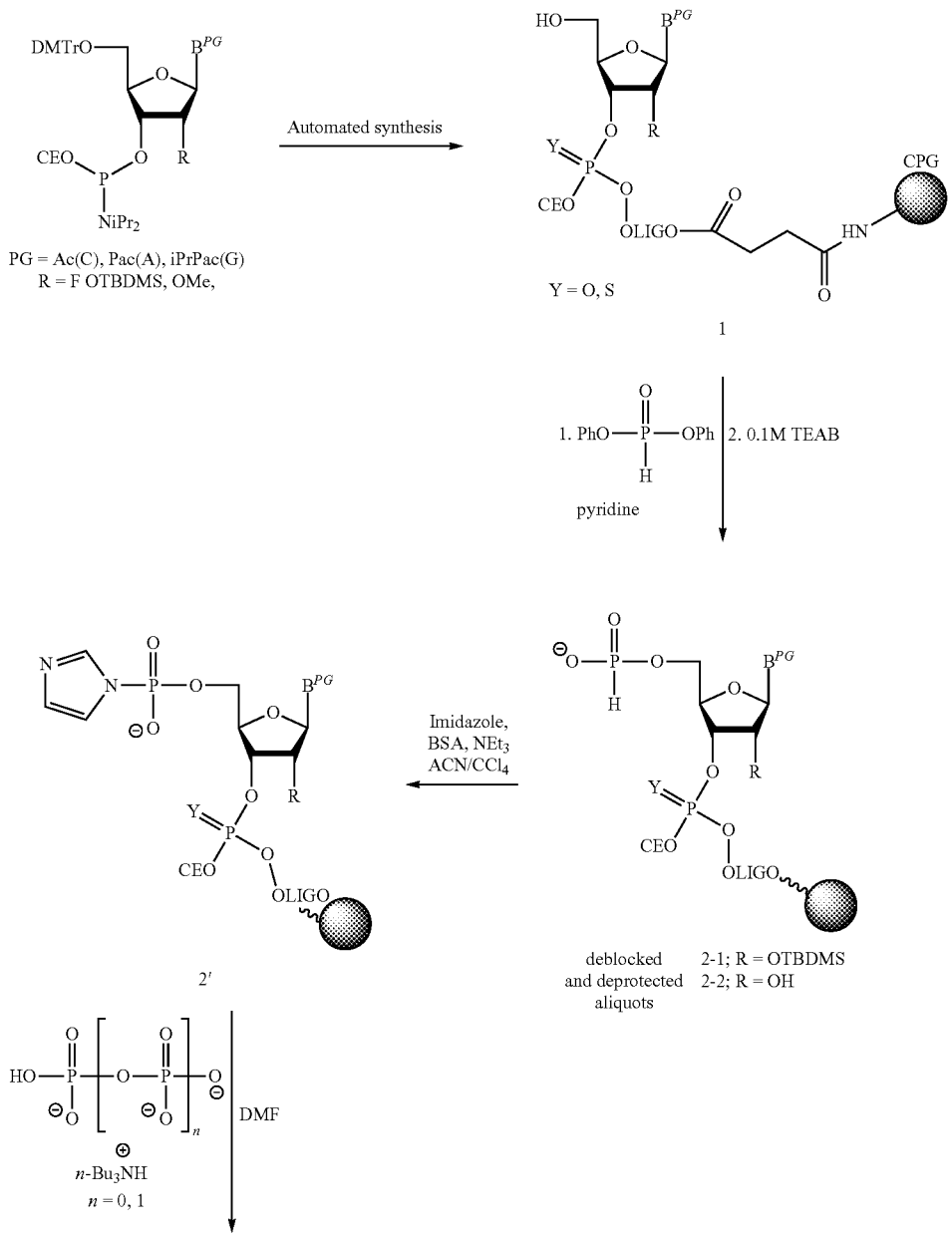

-continued

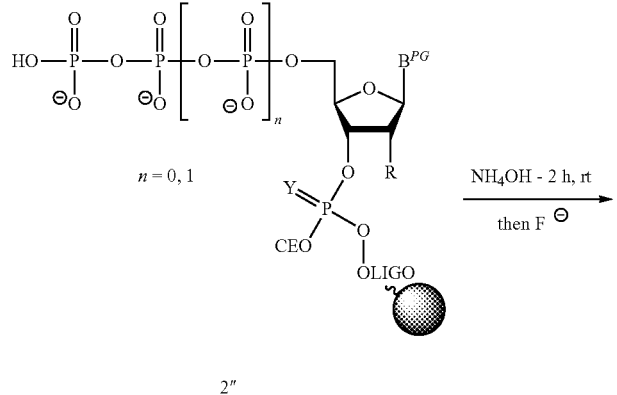 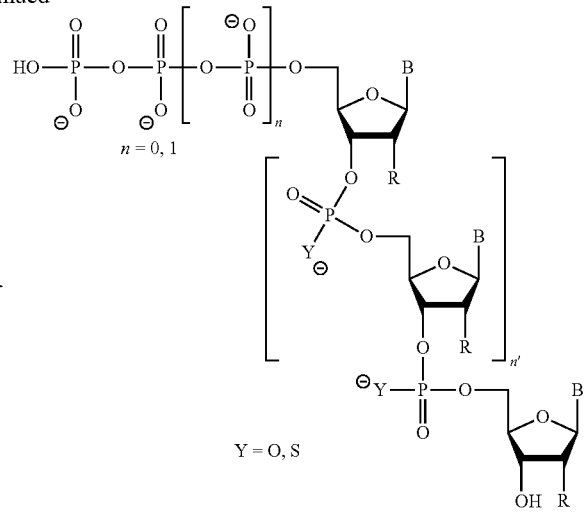

3-1; R = OTBDMS
3-2; R = OH 0.25 - 4 umol of solid supported oligonucleotide 1 (10-60 mg) was placed in a dry Twist oligonucleotide synthesis column (Glen). The column was closed and flushed with argon. A 1M pyridine solution of diphenyl phosphite (misture of 0.4 mL of diphenyl phosphite, Aldrich and 1.6 mL of anhydrous pyridine, Aldrich) was gently pushed through the synthetic column back and forth for 30 minutes at room temperature. The column was then emptied, washed thoroughly with acetonitrile and reverse flushed with argon. 100 mM aqueous TEAB (Aldrich) was then pushed through the column for 2 hours. The column was emptied, washed with anhydrous acetonitrile and reverse flushed with argon. It was then placed under vacuum over $P_2O_5$ for 24 hours, and stocked at -20° C.

2 can be deprotected using aqueous ammonia (JTBaker)/ethanol—3:1 (v/v) for 2 hours at room temperature (2-1), and then 1 M TBAF (Aldrich) treatment for 24 hours at room temperature, desalting and purification (2-2). Solid supported H-Phosphonates 2 (0.25 to 4 umol) were placed in an empty Twist synthesis column. 5 to 6 beads of activated 4 A molecular sieves were introduced inside the column. The column was closed and flushed with argon. The oxidation solution was then prepared as follows: 150 mg (2 mmol) of imidazole (Aldrich) were coevaporated twice with anhydrous acetonitrile and then dried under vacuum over $P_2O_5$. The residue was then redissolved in anhydrous acetonitrile (0.8 mL), anhydrous $CCl_4$ (Aldrich, 0.8 mL), anhydrous triethylamine (Sigma, 0.1 mL) and N,O-bis-trimethylsilyl acetamide (Aldrich, 0.4 mL). The resulting solution was dried over activated 4 A molecular sieves for 10 min, and then degassed with Argon for 30 seconds; it was then pushed gently through the column for 5 hours at room temperature. The column was emptied and washed quickly twice with methanol, then reverse flushed with argon. 1 mL of 0.5 M tris-tributylammonium pyrophosphate (Aldrich, 1 g in 2 mL of anhydrous DMF, Aldrich; dried over activated molecular sieves for 24 h at 4° C.) or 0.5M bis-tributylammonium phosphate (Aldrich, 0.5 g in 2 mL of anhydrous DMF, Aldrich; dried over activated molecular sieves for 24 h at 4° C.) was pushed through the synthesis column for 30 h. The column was then emptied, washed several times with methanol and acetonitrile, followed by reverse flush with argon. The dried solid support CPG carrying the oligonucleotide tri or di phosphates 2" was transferred from the Twist column to an empty screw cap plastic vial (10 mL). 2 mL of 30% $NH_4OH$ (JTBaker)/ethanol-3:1 (v/v) were added and left to react for 2 hours at room temperature. The solution was decanted, evaporated and then lyophilized from water, affording partly or fully deprotected oligonucleotide tri or di phosphates 3-1. Further deprotection of the 2' silyl groups was performed as follows: lyophilized 3-1 was placed in plastic vial and dissolved in 0.5 mL of 1 M TBAF (Aldrich, THF solution). The solution was left to react for 24 hours at room temperature. It was then diluted with 2 mL of water and applied on an equilibrated illustra NAP-25 desalting column (GE Healthcare). It was then eluted with 3.5 mL of water. The solution was collected and lyophilized, affording fully deprotected oligonucleotide tri or di phosphate 3-2. Alternative way for efficient removal of 2'-O-silyl protecting groups was the use of neat $NEt_3$-3HF (Alfa Aesar, 100 μL/μmol) for 48 h at room temperature, followed by precipitation in 3M NaOAc (pH 5.5) and n-butanol, as described by Sproat et al., Nucleosides Nucleotides, 1995, 14, 255. Precipitated RNA TP was washed with cold ethanol, then decanted, dried under vacuum and stored at -20° C. When TBAF was used, further purification-Ion exchange semi-preparative chromatography, followed by semi preparative reverse phase desalting was performed on AKTA purifying system. Conditions were: IE-HPLC semi prep:column: Dionex DNA; gradient (buffer A: 25 mM TRIZMA HCl—Aldrich; buffer B: 25 mM TRIZMA HCl 1 M $NH_4Cl$—Aldrich; 0 to 0.7 M $NH_4Cl$ in 5 CV; flow 10 mL/min). RP-HPLC semi prep:column:C18; gradient (buffer A: 25 mM TEAB—Aldrich; buffer B: Acetonitrile—E. Merck; 0 to 50% acetonitrile in 5 CV; flow 10 mL/min) Collected desalted fraction was freezed and lyophilized, then stored at -20° C.

Scale Up Procedure for 10 umol Synthesis:

10 umol of oligonucleotide supported on CPG (250-300 mg) was placed in an empty dry Twist 10 umol oligonucleotide synthesis column (Glen). The column was closed and flushed with argon. A 1 M pyridine solution of diphenyl phosphite (mixture of 2.0 mL of diphenyl phosphite, Aldrich and 8.0 mL of anhydrous pyridine, Aldrich) was gently pushed through the synthetic column back and forth for 30 minutes at room temperature. The column was then emptied, washed thoroughly with acetonitrile and reverse flushed with argon. 100 mM aqueous TEAB (10 mL, Aldrich) was then pushed through the column for 2 hours. The column was emptied, washed with anhydrous acetonitrile and reverse flushed with argon. It was then placed under vacuum over $P_2O_5$ for 24 hours, and stocked at −20° C.

2 can be deprotected using aqueous ammonia (JTBaker)/ethanol—3:1 (v/v) for 2 hours at room temperature (2-1), and then 1 M TBAF (Aldrich) treatment for 24 hours at room temperature, desalting and purification (2-2). Solid supported H-Phosphonates 2 (10 umol) were placed in an empty Twist 10 umol synthesis column. 5 to 6 beads of activated 4 A molecular sieves are introduced inside the column. The column was closed and flushed with argon. The oxidation solution was then prepared as follows: 1.50 g (20 mmol) of imidazole (Aldrich) were coevaporated twice with anhydrous acetonitrile and then dried under vacuum over $P_2O_5$. The residue was then redissolved in anhydrous acetonitrile (4 mL), anhydrous $CCl_4$ (Aldrich, 4 mL), anhydrous triethylamine (Sigma, 0.5 mL) and N,O-bis-trimethylsilyl acetamide (Aldrich, 2.0 mL). The resulting solution was dried over activated 4 A molecular sieves for 10 min, and then degassed with Argon for 30 seconds; it was then pushed gently through the column for 5 hours at room temperature. The column was emptied and washed quickly twice with methanol, then reverse flushed with argon. 1 mL of 0.5 M tris-tributylammonium pyrophosphate (Aldrich, 3 g in 6 mL of anhydrous DMF, Aldrich; dried over activated molecular sieves for 24 h at 4° C.) or 0.5M bis-tributylammonium phosphate (Aldrich, 0.5 g in 2 mL of anhydrous DMF, Aldrich; dried over activated molecular sieves for 24 h at 4° C.) was pushed through the synthesis column for 30 h. The column was then emptied, washed several times with methanol and acetonitrile, followed by reverse flush with argon. The dried solid support CPG carrying the oligonucleotide tri or di phosphates 2″ was transferred from the Twist column to an empty screw cap plastic vial (10 mL). 10 mL of 30% $NH_4OH$ (JTBaker)/ethanol—3:1 (v/v) were added and left to react for 2 hours at room temperature. The solution was decanted, evaporated and then lyophilized from water, affording partly or fully deprotected oligonucleotide tri or di phosphates 3-1. Further deprotection of the 2′ silyl groups was performed as follows: lyophilized 3-1 was placed in plastic vial and dissolved in 5 mL of 1 M TBAF (Aldrich, THF solution). The solution was left to react for 24 hours at room temperature. It was then diluted with water and desalted by RP C18 semi preparative HPLC an AKTA purifying unit. The fractions were collected and lyophilized, affording fully deprotected oligonucleotide tri or di phosphate 3-2. Alternative way for efficient removal of 2′-O-silyl protecting groups was the use of neat $NEt_3$-3HF (Alfa Aesar, 100 μL/μmol) for 48 h at room temperature, followed by precipitation in 3M NaOAc (pH 5.5) and n-butanol, as described by Sproat et al., Nucleosides Nucleotides, 1995, 14, 255. Precipitated RNA TP was washed with cold ethanol, then decanted, dried under vacuum and stored at −20° C.

3. Duplex Annealing for the Synthesis of dsRNAi-5′ Tri or Di Phosphates, and 5′ Alpha-Thio Tri or Di Phosphates:

The complementary sequence strands of all target oligonucleotides 3 were synthesized on solid support CPG using standard oligoribonucleotide synthesis employing the commercially available 2′O-TBDMS 3′ phosphoramidite building blocks. After deblocking with ammonia and removal of the 2′OTBDMS groups using the 3HF-$NEt_3$ complex, the oligonucleotides were purified by ion exchange HPLC then desalted on reverse phase HPLC and lyophilized from water.

dsRNAi were generated by annealing an equimolar amounts of complementary sense and antisense strands.

Biochemistry Assays

1. Recognition of RNA 5′ Triphosphates and its Analogs by RIG-1Helicase. RIG-I Activation and IFN-Alpha Induction:

As described by Hornung et al. (Science, 2006, 314, 994), 5′ triphosphate RNA was the ligand for retinoic acid-inducible protein I (RIG-I), a key sensor of viral infections. The activation of the latter induces activation of IFN cytokines. Purified monocytes were stimulated with single-stranded or double-stranded synthetic or in vitro-transcribed RNA oligonucleotide 5′ triphosphates as described by Scheele et al. (Immunity, 2009, 31, 25). Human PBMCs were isolated from whole human blood of healthy, voluntary donors by Ficoll-Hypaque density gradient centrifugation. Plasmacytoid dendritic cells (PDCs) were positively depleted with magnetically labeled anti-CD304 antibody (Miltenyi Biotec). Untouched monocytes were obtained by negative depletion from PBMCs according to the manufacturer's instructions (Human Monocyte Isolation Kit II, Miltenyi Biotec). Cells were kept in RPMI 1640 containing 10% FCS, 1.5 mM L-glutamine, 100 U/ml penicillin, and 100 μg/ml streptomycin. All compounds were tested for endotoxin contamination prior to use. Mouse embryonic fibroblasts (MEFs) from MDA-5$^{-/-}$, RIG-I$^{-/-}$, and IPS-1$^{-/-}$ mice were prepared as described (Kato et al., 2006, Nature, 441, 101). For transfection, 0.2 ug nucleic acid and 0.5 ul Lipofectamine (Invitrogen) were mixed in 50 ul Optimem (Invitrogen), incubated for 20 mM, and added to the well containing 200,000 cells.

The amount of IFN-α production was determined with the IFN-α module set from Bender MedSystems. The ELISA assay was performed according to the manufacturer's protocol. The concentration of cytokines was determined by standard curve obtained using known amounts of recombinant cytokines.

$(His_6)$-Flag-tagged RIG-I (HF-RIG-I) ("$His_6$" disclosed as SEQ ID NO: 17) was transiently overexpressed in 293T cells and lysed in a CHAPS containing lysis buffer (150 mM NaCl, 50 mM Tris/HCl [pH 7.4], 2 mM $MgCl_2$, 1 mM DTT, and 1% CHAPS) including protease inhibitor cocktail (Roche). The lysate was incubated over night at 4° C. with anti-FLAG beads (Sigma). Anti-FLAG beads were washed subsequently with lysis buffer and high-salt ish buffer (300 mM NaCl, 50 mM Tris/HCl [pH 7.4], 5 mM $MgCl_2$, 1 mM DTT, and 0.1% CHAPS). RIG-1-FLAG was eluted by an addition of FLAG-peptide (300 ug/ml) solution to the beads. Purity of recombinant RIG-I was determined by SDS-PAGE separation and subsequent Coomassie blue staining.

The binding affinity of RNA for $(His_6)$FLAG-tagged RIG-I (HF-RIG-I) ("$His_6$" disclosed as SEQ ID NO: 17) was determined as described ([Haas et al., 2008, Immunity, 28, 315] and [Latz et al., 2007, Nat. Immun., 8, 772]) by an amplified luminescent proximity homogenous assay (AlphaScreen; PerkinElmer). In this assay, purified HF-RIG-I was incubated with increasing concentrations of biotinylated RNA for 1 hr at 37° C. in buffer (50 mM Tris [pH 7.4], 100 mM NaCl, 0.01% Tween20, and 0.1% BSA) and subsequently incubated for 30 min at 25° C. with HF-RIG-1-binding Nickel Chelate Acceptor Beads (PerkinElmer) and biotin-RNA-binding Streptavidin donor beads (PerkinElmer). The donor bead contains the photosensitizer phthalocyanine, which converts ambient oxygen into a "singlet" oxygen after illumination with a 680 nm laser light. During the 4 ms lifetime, the "singlet" oxygen can diffuse up to 200 nm and activate a thioxene derivative on the acceptor bead that was brought into proximity by interaction of the test molecules bound to the beads. The resulting chemiluminescence with subsequent activation of a fluorochrome (contained within the same bead) emitting in the range of 520-620 nm correlates with the number and proximity of associated beads that was inversely correlated with the dissociation constant of donor (biotin-RNA) and acceptor (HF-RIG-I). The assay was performed in wells of 384-well plates (Proxiplate; PerkinElmer). Plates were analyzed for emitted fluorescence with a multilabel reader (Envision; PerkinElmer).

2. Synergic Effect of RIG-I Activation and mRNA Silencing Using Oligonucleotide 5' Triphosphates or Analogs:

As described by Poeck et al. (Nat. Med., 2007, 14, 1256), oligonucleotide with 5' triphosphate ends can successfully synergize the RIG-I mediated immune response triggering, with the oligonucleotide mediated silencing of targeted mRNAs. As an example, the Bcl2 mRNA can be targeted by the appropriate oligonucleotide, inducing silencing of the Bcl2 protein which, along with RIG-I mediated immune response activation, provokes massive apoptosis of tumor cells in lung metastases in vivo (Nat. Med., 2007, 14, 1256).

Melanoma cells, melanocytes and fibroblasts with RNAs (1 mg ml 1) were transfected for 24 h with Lipofectamine 2000 or Lipofectamine RNAiMAX (both from Invitrogen) according to the manufacturer's protocol. Dendritic cells were transfected as well as enriched lymphocyte subsets with 200 ng of nucleic acid with 0.5 ml of Lipofectamine in a volume of 200 ml. Female C57BL/6 and BALB/c mice were used. Mice are 6-12 weeks of age at the beginning of the experiments. For tumor treatment, Tlr7- or Ifnar1-deficient mice were used that are crossed into the C57BL/6 genetic background for at least ten generations. RNAs were intravenously injected after complexation with in vivo-jetPEI (201-50, Biomol) according to the manufacturer's protocol. For systemic dendritic cell depletion, CD11c-DTR transgenic mice were injected intraperitoneally with 100 ng of diphtheria toxin in PBS (Sigma D-0564). Lung metastasis was experimentally induced by injection of 4_105 B16 melanoma cells into the tail vein. For tumor treatment, 50 mg of RNA complexed with jetPEI was administered in a volume of 200 ml on days 3, 6 and 9 after tumor challenge by retroorbital or tail vein injection. Fourteen days after tumor challenge, the number of macroscopically visible melanoma metastases was counted on the surface of the lungs.

To confirm efficient gene silencing in vitro and in vivo, western blot analyses were performed with lysed tumor cells and tumor tissue, flow cytometric analyses with single-cell suspensions, and quantitative RT-PCR and 5c-RACE analyses with extracted total RNA. For rescue experiments, B16 melanoma cells were transfected stably with a mutated Bcl2 cDNA specifically designed to disrupt the target cleavage site of the Bcl2-specific oligonucleotide 2.2 without affecting the amino acid sequence of the Bcl-2 protein.

The production of cytokines in culture supernatants was measured by ELISA, and then the activation of dendritic cells and NK cells was assessed by flow cytometry and the stimulation of NK cell lytic activity against tumor cells was determined with a standard 51Cr release assay. To determine the activation of type I IFN in tumor cells, a luciferase-based IFN-b reporter gene assay was used.

The induction of apoptosis in cells cultured in vitro or freshly isolated ex vivo was measured by staining for annexin the cell surface and by using flow cytometry. Alternatively, viable cells were quantified with a fluorometric assay (Cell-Titer-Blue Cell Viability Assay, Promega) in vitro. Apoptosis was further verified in vivo by immunohistochemistry with TUNEL staining.

3. Production of GpppX 5' capped RNA:

In order to get GpppX-capped RNAs, several approaches can be taken that differ widely in their efficiency. They can be synthesized chemically starting from mono- or diphosphate RNA. A $^{7Me}$GpppA cap can also be added to di- or triphosphate RNA using vaccinia virus capping enzyme that contains RNA triphosphatase, guanylyltransferase and N7MTase activities (Peyrane et al., Nucl. Acid Res., 2007, 35, e26; Brownlee et al., Nucl. Acid. Res., 1995, 23, 2641; Shuman, J. Biol. Chem., 264, 9690).

Guanylyltransferase: Reaction mixtures (20 uL) containing 50 mM Tris-HCl, pH 7.5, 5 mM DTT, 1.25 mM MgCl$_2$, 25 uM [α-$^{32}$P] GTP (9900 cpm/μmol), 39 μmol (of 5' ends) triphosphate-terminated RNA oligonucleotide, and 2 uL of enzyme were incubated for 30 min at 37° C. Reactions were halted by the addition of 5% trichloroacetic acid, and acid-insoluble material was collected by filtration. The filters were counted in liquid scintillation fluid. Capping and 32P-labeling of phosphorylated oligonucleotides: Capping of the RNA 5' triphosphates using 1 U guanylyl transferase (Gibco BRL) and 1 uM [α-$^{32}$P]GTP (3000 Ci/mmol; Amersham) in 0.05 M Tris-HCl, pH 7.8, 1.25 mM MgCl$_2$, 6 mM KCl, 2.5 mM dithiothreitol, 20 U human placental ribonuclease inhibitor (Promega), 0.1 mM S-adenosylmethionine in a 5, 1 reaction volume for 1 h at 37° C. In some experiments bovine serum albumin (0.4 ug) was added. The reaction products were analysed, or in preparative experiments purified, by electrophoresis on 20% polyacrylamide-7 M urea gels. The major radioactive band were detected by autoradiography and eluted in 0.25 M ammonium acetate, as above. The eluate was centrifuged to remove gel pieces and the RNA precipitated from the supernatant with 3 vol ethanol in the presence of 2 M ammonium acetate and 20 ug yeast carrier RNA.

Methods for Identifying Oligonucleotides with Ability to Inhibit or Stimulate the Immune System.

Modulation of the immune system can be measured for example by (i) measurement of either the mRNA or protein expression levels of a component (e.g., a growth factor, cytokine, or interleukin) of the immune system, e.g., in a cell or in an animal, (ii) measurement of the mRNA or protein levels of a protein factor activated by a component of the immune system (for example, NFKB), e.g., in a cell or in an animal, (iii) measurement of cell proliferation, e.g., in a tissue explant or a tissue of an animal.

Evaluation of the oligonucleotide can include incubating the modified strand (with or without its complement, but preferably annealed to its complement) with a biological system, e.g., a sample (e.g, a cell culture). The biological sample can be capable of expressing a component of the immune system. This allows identification of an oligonucleotide that has an effect on the component. In one embodiment, the step of evaluating whether the oligonucleotide modulates, e.g, stimulates or inhibits, an immune response includes evaluating expression of one or more growth factors, such as a cytokine or interleukin, or cell surface receptor protein, in a cell free, cell-based, or animal assay. Protein levels can be assayed, for example, by Western blot techniques, flow cytometry, or reporter gene expression (e.g., expression of a fluorescent reporter protein, such as green fluorescent protein (GFP)). The levels of mRNA of the protein of interest can be measured by Northern blot techniques, RNAse Protection Assays, or Quality Control-PCR (QC-PCR) (including quantitative reverse transcription coupled PCR (RT-PCR)) and analogous methods known in the art. RNA and/or protein levels resulting from target gene expression can be measured at regular time intervals following introduction of the test oligonucleotide, and the levels are compared to those following introduction of a control oligonucleotide into cells.

In one embodiment, the step of testing whether the modified oligonucleotide modulates, e.g., stimulates, an immune response includes assaying for an interaction between the oligonucleotide and a protein component of the immune system, e.g., a growth factor, such as a cytokine or interleukin, or a cell surface receptor protein. Exemplary assay methods include coimmunoprecipitation assays, bead-based co-isolation methods, nucleic acid footprint assays and colocalization experiments such as those facilitated by immunocytochemistry techniques.

Cell proliferation can be monitored by following the uptake of [$^3$H]thymidine or of a fluorescent dye. Cells are plated in a 96-well tissue culture plate and then incubated with the oligonucleotide. For radiometric analysis, [$^3$H]thymidine is added and incubation is continued. The cells are subsequently processed on a multichannel automated cell harvester (Cambridge Technology, Cambridge, Mass.) and counted in a liquid scintillation beta counter (Beckman Coulter). For fluorescence-based analysis, a commercially available assay, like the LIVE/DEAD Viability/Cytotoxicity assay from Molecular Probes can be used. The kit identifies live versus dead cells on the basis of membrane integrity and esterase activity. This kit can be used in microscopy, flow cytometry or microplate assays.

A number of embodiments of the invention have been described. Nevertheless, it will be understood that various modifications may be made without departing from the spirit and scope of the invention. Other embodiments are in the claims.

What is claimed is:

1. A process for preparing an oligonucleotide 5'-triphosphate, comprising the steps of:
   (a) synthesizing an oligonucleotide having a 5' hydroxyl moiety;
   (b) reacting the 5' hydroxyl moiety with a reagent of formula I:

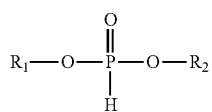
   (I)

wherein $R_1$ and $R_2$ are each independently selected from the group consisting of haloalkyl, aryl, substituted aryl, heteroaryl, substituted heteroaryl, cycloalkyl, substituted cycloalkyl, heterocycle, substituted heterocycle, acyl, phosphoryl, substituted alkyl acyl, substituted heteroalkyl acyl, substituted aryl acyl or substituted heteroaryl acyl, substituted alkyl phosphoryl, substituted heteroalkyl acyl, substituted aryl phosphoryl, and substituted heteroaryl phosphoryl,
   to convert the 5' hydroxyl moiety to a 5'-H-phosphonate;
   (c) activating the H-phosphonate of step (b) by reacting the H-phosphonate with a silylating agent, a halogenated oxidizing agent, a nitrogen-containing heteroaryl compound, or a combination thereof, to form an activated H-phosphonate; and
   (d) treating the oligonucleotide having an activated H-phosphonate from step (c) with a poly(alkylammonium)pyrophosphate;
   to produce an oligonucleotide 5'-triphosphate,
   wherein in each occurrence, the substituted group is independently selected from the group consisting of alkyl, alkenyl, alkynyl, alkoxy, halo, hydroxy, cyano, nitro, azido, amino, $SO_3H$, sulfate, phosphate, perfluoroalkyl, perfluoroalkoxy, methylenedioxy, ethylenedioxy, carboxyl, oxo, thioxo, imino (alkyl, aryl, and aralkyl), $S(O)_{0-2}$ alkyl, $S(O)_{0-2}$ aryl, $S(O)_{0-2}$ heteroaryl, $S(O)_{0-2}$ heterocyclyl, amino (mono-, di-, alkyl, cycloalkyl, aralkyl, heteroaralkyl, or combinations thereof), carboxylic acid ester (alkyl, aralkyl, or heteroaralkyl), carboxamido (mono-, di-, alkyl, aralkyl, heteroaralkyl, or combinations thereof), sulfonamido (mono-, di-, alkyl, aralkyl, heteroaralkyl, or combinations thereof), aryl, heteroaryl, heterocyclyl, and cycloalkyl.

2. The method of claim 1, wherein the oligonucleotide synthesis method is selected from the group consisting of solid phase phosphoramidite, solution phase phosphoramidite, solid phase H-phosphonate, solution phase H-phosphonate, hybrid phase phosphoramidite, hybrid phase H-phosphonate, and combinations and derivations thereof.

3. The method of claim 1, wherein the reacting step (b) further comprises an aqueous base treatment.

4. The process of claim 1, wherein the nitrogen-containing heteroaryl compound is substituted or unsubstituted, and selected from the group consisting of pyridine, imidazole, triazole, and tetrazole.

5. The process of claim 1, wherein the poly(alkylammonium)pyrophosphate is selected from the group consisting of tris(tri-n-butylammonium)pyrophosphate; tetrakis(tri-n-butylammonium)pyrophosphate; tris(tetra-n-butylammonium)pyrophosphate; and tetrakis(tetra-n-butylammonium)pyrophosphate.

6. The process of claim 1, wherein the oligonucleotide having a 5' hydroxyl moiety obtained from step (a) further comprises at least one protecting group and/or a solid support.

7. The process of claim 6, wherein at least one of the protecting groups is a 2' protecting group selected from the group consisting of alkysilyl,

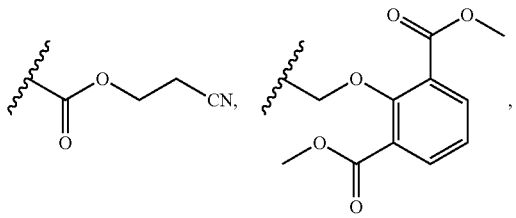

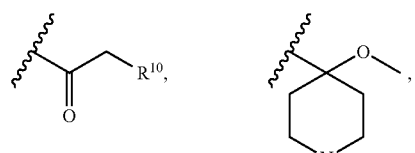

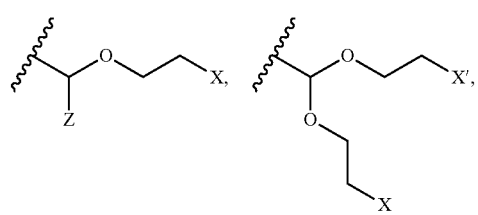

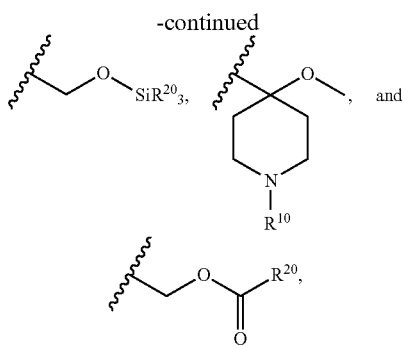

wherein X and X' are independently CN, $NO_2$, $CF_3$, F, or OMe; Z is H or alkyl; $R^{10}$ is aryl, substituted aryl, heteroaryl or substituted heteroaryl; and $R^{20}$ is alkyl.

8. The process of claim 7, wherein at least one of the 2' protecting groups is t-butyldimethylsilyl (TBDMS) or $CH_2O(CO)$-t-butyl.

9. The method of claim 7, wherein the method further comprises the step of:
(e) removing the protecting group(s) and/or removing the oligonucleotide 5'-triphosphate product from the solid support.

10. The method of claim 1, wherein the method takes place in the absence of an enzyme.

11. A process for preparing an oligonucleotide 5'-triphosphate, comprising the steps of:
(a) synthesizing an oligonucleotide having a 5' hydroxyl moiety;
(b) reacting the 5' hydroxyl moiety with a reagent of formula II:

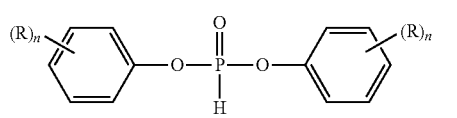

(II)

wherein R is each independently hydrogen, halogen, haloalkyl, halogen, $NO_2$, CN, acyl, sulfonyl, aryl, substituted aryl, heteroaryl, substituted heteroaryl, cycloalkyl, substituted cycloalkyl, heterocycle, or substituted heterocycle, and each n is 0 to 5,
to convert the 5' hydroxyl moiety to a 5'-H-phosphonate;
(c) activating the H-phosphonate of step (b) by reacting the H-phosphonate with a silylating agent, a halogenated oxidizing agent, a nitrogen-containing heteroaryl compound, or a combination thereof, to form an activated H-phosphonate; and
(d) treating the oligonucleotide having an activated H-phosphonate from step (c) with a poly(alkylammonium)pyrophosphate;
to produce an oligonucleotide 5'-triphosphate,
wherein in each occurrence, the substituted group is independently selected from the group consisting of alkyl, alkenyl, alkynyl, alkoxy, halo, hydroxy, cyano, nitro, azido, amino, $SO_3H$, sulfate, phosphate, perfluoroalkyl, perfluoroalkoxy, methylenedioxy, ethylenedioxy, carboxyl, oxo, thioxo, imino (alkyl, aryl, and aralkyl), $S(O)_{0-2}$ alkyl, $S(O)_{0-2}$ aryl, $S(O)_{0-2}$ heteroaryl, $S(O)_{0-2}$ heterocyclyl, amino (mono-, di-, alkyl, cycloalkyl, aralkyl, heteroaralkyl, or combinations thereof), carboxylic acid ester (alkyl, aralkyl, or heteroaralkyl), amide (mono-, di-, alkyl, aralkyl, heteroaralkyl, or combinations thereof), sulfonamido (mono-, di-, alkyl, aralkyl, heteroaralkyl, or combinations thereof), aryl, heteroaryl, heterocyclyl, and cycloalkyl.

12. The method of claim 11, wherein the oligonucleotide synthesis method is selected from the group consisting of solid phase phosphoramidite, solution phase phosphoramidite, solid phase H-phosphonate, solution phase H-phosphonate, hybrid phase phosphoramidite, hybrid phase H-phosphonate, and combinations and derivations thereof.

13. The method of claim 11, wherein the reacting step further comprises an aqueous base treatment.

14. The process of claim 11, wherein the nitrogen-containing heteroaryl compound is substituted or unsubstituted, and selected from the group consisting of pyridine and imidazole.

15. The process of claim 11, wherein the poly(alkylammonium)pyrophosphate is tris(tri-n-butylammonium)pyrophosphate.

16. The process of claim 11, wherein n is 0.

17. The process of claim 11, wherein the oligonucleotide having a 5' hydroxyl moiety obtained from step (a) further comprises at least one protecting group and/or a solid support.

18. The process of claim 17, wherein at least one of the protecting groups is a 2' protecting group selected from the group consisting of alkysilyl,

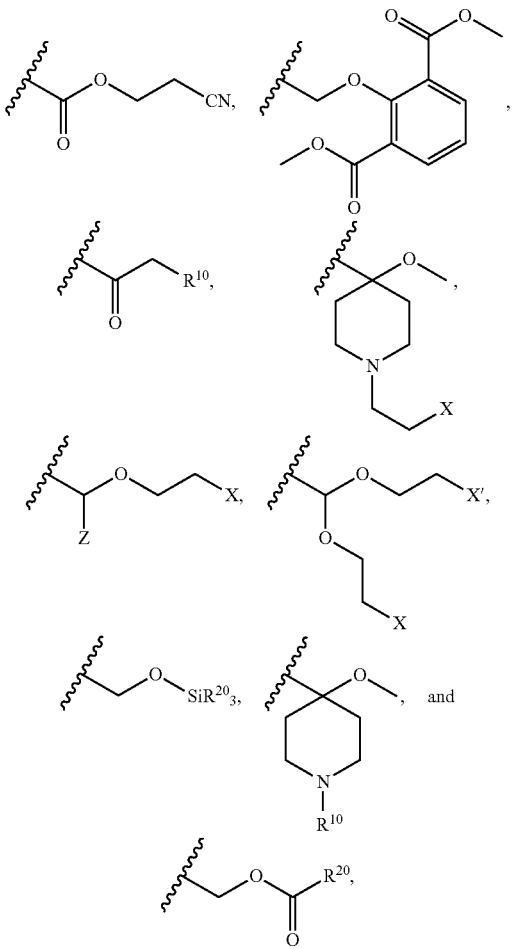

wherein X and X' are independently CN, $NO_2$, $CF_3$, F, or OMe; Z is H or alkyl; $R^{10}$ is aryl, substituted aryl, heteroaryl or substituted heteroaryl; and $R^{20}$ is alkyl.

19. The process of claim 18, wherein at least one of the 2' protecting groups is TBDMS or $CH_2O(CO)$-t-butyl.

20. The method of claim 18, wherein the method further comprises the step of:
   (e) removing the protecting group(s) and/or removing the oligonucleotide 5'-triphosphate product from the solid support.

21. The method of claim 11, wherein the method takes place in the absence of an enzyme.

* * * * *